(12) United States Patent
Szymczak et al.

(10) Patent No.: US 10,519,172 B2
(45) Date of Patent: Dec. 31, 2019

(54) COMPLEXES FOR NUCLEOPHILIC, RADICAL, AND ELECTROPHILIC POLYFLUOROALKYLATION

(71) Applicant: THE REGENTS OF THE UNIVERSITY OF MICHIGAN, Ann Arbor, MI (US)

(72) Inventors: Nathaniel Szymczak, Ypsilanti, MI (US); Jacob Geri, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 16/308,304

(22) PCT Filed: Jun. 23, 2017

(86) PCT No.: PCT/US2017/038943
§ 371 (c)(1),
(2) Date: Dec. 7, 2018

(87) PCT Pub. No.: WO2017/223406
PCT Pub. Date: Dec. 28, 2017

(65) Prior Publication Data
US 2019/0127397 A1    May 2, 2019

Related U.S. Application Data

(60) Provisional application No. 62/353,928, filed on Jun. 23, 2016.

(51) Int. Cl.
C07F 5/05        (2006.01)
C07B 39/00      (2006.01)
C07B 37/02      (2006.01)
C07B 47/00      (2006.01)
C07C 17/278    (2006.01)
C07C 29/64      (2006.01)
C07C 209/52    (2006.01)

(52) U.S. Cl.
CPC ............... *C07F 5/05* (2013.01); *C07B 37/02* (2013.01); *C07B 39/00* (2013.01); *C07B 47/00* (2013.01); *C07C 17/278* (2013.01); *C07C 29/64* (2013.01); *C07C 209/52* (2013.01); *Y02P 20/582* (2015.11)

(58) Field of Classification Search
None
See application file for complete search history.

(56) References Cited

U.S. PATENT DOCUMENTS 3,335,180 A    8/1967 Faust et al.
5,612,013 A    3/1997 Sneddon et al.
2004/0230079 A1    11/2004 Prakash et al.
(Continued)

OTHER PUBLICATIONS

Barata-Vallejo (referred to herein as "Barata", "Recent Advances in Trifluoromethylation Reactions with Electrophilic Trifluoromethylating Reagents" Chemistry, a European Journal, 2014, 20, p. 16806-16829) (Year: 2014).*

(Continued)

*Primary Examiner* — Amy C Bonaparte
(74) *Attorney, Agent, or Firm* — Marshall, Gerstein & Borun LLP

(57) ABSTRACT

Disclosed herein are borazine complexes and use of the same in perfluoroalkylation reactions.

19 Claims, 9 Drawing Sheets

(56) References Cited

U.S. PATENT DOCUMENTS

2014/0066640 A1* 3/2014 Prakash ............... C07C 29/40
549/497

OTHER PUBLICATIONS

Kolomeitsev ("Perfluoroalkyl borates and boronic esters: new promising partners for Suzuki and Petasis reactions" Tetrahedron Letters, 44, 2003, p. 8273-8277) (Year: 2003).*
Knauber ("Copper-Catalyzed Trifluoromethylation of Aryl Iodides with Potassium (Trifluoromethyl)trimethoxyborate" Chem. Eur. J, 2011, 17, po. 2689-2697) (Year: 2011).*
Srivastava ("The aromaticity and electronic properties of monosubstituted benzene, borazine, and diazadiborine rings: an ab initio MP2 study", Theoretical Chemistry Accounts, 2016, vol. 135, p. 1-7) (Year: 2016).*
Levin ("Nucleophilic trifluoromethylation with organoboron reagents" Tetrahedron Letters, 2010, 52, p. 281-284) (Year: 2010).*
International Preliminary Report on Patentability, PCT/US2017/038943 (dated Dec. 25, 2018).
International Search Report and Written Opinion, PCT/US2017/038943 (dated Nov. 9, 2017).
Khan et al., Oxidative trifluoromethylation of arylboronates with shelf-stable potassium (trifluoromethyl)trimethoxyborate, *Chemistry*. 18:1577-87 (2012).
Srivastava et al., The aromaticity and electronic properties of monosubstituted benzene borazine and diazadiborine rings: an ab into MP2 study, *Theoretical Chemistry Accounts*. 135:1-7 (2016).

* cited by examiner

Nucleophilic Aromatic Substitution

Direct Dearomatizing Nucleophilic Addition

Quinazoline Bistrifluoromethylation

Triazine Bistrifluoromethylation

Iterative Synthesis of $CF_3^-$ Reagent

Net Reaction:

In-Situ LA Recycling:

Figure 4 Cont. Synthesis of $CF_3\bullet$ Reagent with LA Recovery
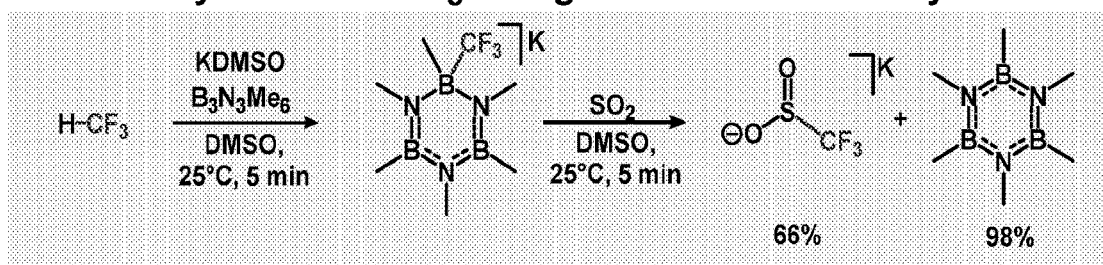
Synthesis of $CF_3^+$ Reagent with In-Situ Use
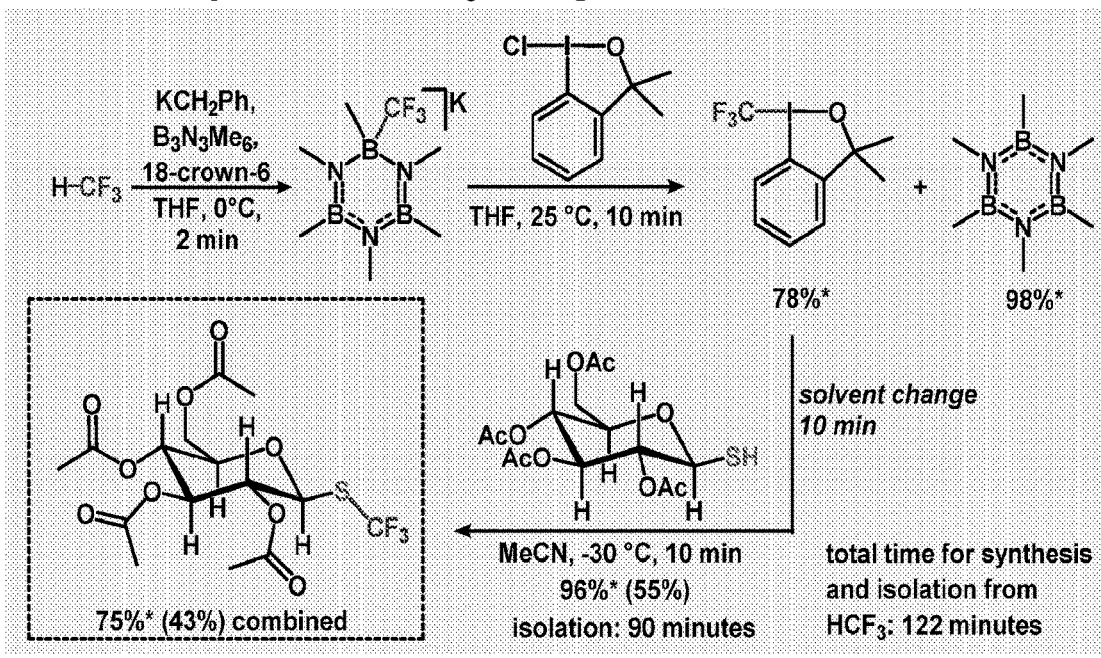

COMPLEXES FOR NUCLEOPHILIC, RADICAL, AND ELECTROPHILIC POLYFLUOROALKYLATION

STATEMENT OF GOVERNMENT SUPPORT

This invention was made with government support under grant number Fo35579, awarded by the National Science Foundation. The government has certain rights in the invention.

BACKGROUND

The conversion of chemical waste streams into valuable complex molecules is a grand challenge in chemical synthesis. One of the most underutilized waste streams is fluoroform ($HCF_3$), a potent greenhouse gas and a byproduct of the Teflon industry. Although this gas contains the trifluoromethyl functional group ($CF_3$), whose extreme lipophilicity and resistance to degradation makes it indispensable in medicinal chemistry, it is currently incinerated rather than used as a $CF_3$ feedstock because of its strong C—H bond and unstable $CF_3^-$ anion. Additionally, current methods for installing the $CF_3$ group in organic molecules generate substantial waste byproducts, present significant operational challenges, and are cost-prohibitive in large-scale applications. For these reasons, a longstanding goal in synthetic chemistry has been the development of new trifluoromethylation reagents with: (1) economic preparation at ambient temperature from $HCF_3$, (2) very high inherent reactivity, and (3) minimal waste generation. Disclosed herein is a $CF_3^-$ transfer reagent satisfying these criteria, developed through the application of a new conceptual framework. The prior state of the art for the transformation of $HCF_3$ into useful trifluoromethylation reagents required the use of expensive bulky bases and strong Lewis acids (LA). These reagents must be irreversibly activated prior to $CF_3^-$ transfer, resulting in destruction of the Lewis acid and generation of stoichiometric waste. It is shown that a highly reactive $CF_3^-$ adduct can be synthesized from alkali metal hydride, HCF3, and borazine Lewis acids in quantitative yield at room temperature. The reagents possess Grignard-like nucleophilicity and thermal stability without additional chemical activation, and after $CF_3^-$ transfer the free borazine is quantitatively regenerated. These features expand the scope of nucleophilic trifluoromethylation to new classes of substrates and enable rapid (<30 minute) synthesis of popular nucleophilic, radical, and electrophilic trifluoromethylation reagents with complete recycling of the borazine Lewis acid.

The trifluoromethyl functional group is widely used in medicinal chemistry to enhance the bioavailability, lipophilicity, and resistance to oxidative degradation of drug molecules. However, the trifluoromethylation of complex organic compounds is difficult because of the instability of isolated $CF_3$ fragments, generally low reactivity of $CF_3$ ligands in organometallic cross-coupling, and the absence of any synthetic biology approaches for its incorporation. Unlike other alkyl groups, which can be readily transferred to electrophilic substrates using robust organolithium and Grignard reagents, analogous $LiCF_3$ and $MgCF_3$ reagents are not stable because they irreversibly eliminate fluoride at −80° C. However, $CF_3^-$ can be stabilized through the formation of a Lewis acid (LA)-$CF_3$ adduct; this strategy forms the basis of all popularly used nucleophilic, radical, and electrophilic trifluoromethylation reagents.

Unfortunately, $CF_3^-$ reagents stabilized by strong Lewis acids lack the synthetic versatility, economic preparation, and atom efficiency needed for large-scale use. Strong LA-$CF_3$ adducts such as $SiMe_3CF_3$ possess little inherent reactivity and must be irreversibly activated with exogenous nucleophiles (e.g. F—) to effect $CF_3$ transfer, resulting in stoichiometric waste byproducts. Despite twenty years of optimization, the cost of common LA-CF3 reagents still limits their use in large-scale processes.

Fluoroform ($HCF_3$), a byproduct of Teflon manufacturing (<$0.10/mole), is an attractive alternative starting material for preparing $CF_3$ transfer reagents. If $HCF_3$ and recyclable Lewis acids could be used to generate LA-$CF_3$ reagents in economically efficient, single-step reactions that generate minimal waste, it may dramatically lower the cost of synthesizing trifluoromethylated drug compounds. In addition to simultaneously reducing the cost of the trifluoromethyl group in large-scale processes and putting a greenhouse gas to productive use, this strategy could also present opportunities for expanding the scope of trifluoromethylation reactions.

The trifluoromethyl functional group is ubiquitous in drugs and fine chemicals. The unstable anion $CF_3$— is a common intermediate in nucleophilic trifluoromethylation reactions, and its stabilization by strong silane Lewis acids has enabled the design of successful $CF_3$— reagents. However, these reagents remain expensive because their synthesis from cheap $HCF_3$ has demanded strong, bulky amide or phosphazene bases capable of both deprotonating $HCF_3$ and avoiding adduct formation with the strong Lewis acids needed to stabilize the $CF_3^-$ anion. Additionally, their use generates unavoidable silicon-containing waste products because the release of reactive $CF_3^-$ is triggered by the irreversible formation of a strong Si—O or Si—F bond. If reactive and recyclable $CF_3^-$ reagents could be synthesized using low-cost $HCF_3$ and simple alkoxide or hydride bases, it could lead to a significant reduction in the cost of installing the trifluoromethyl group. It is shown herein that a highly reactive, but stable, $CF_3^-$ adduct can be synthesized from potassium toluide or sodium/potassium hydride, $HCF_3$, and the weak Lewis acid borazine in >95% yield at room temperature. It is a powerful nucleophilic reagent with reactivity strongly resembling a Grignard reagent, allowing it to trifluoromethylate a wide variety of polar unsaturated bonds in organic compounds, electron-deficient aromatic halides and pseudohalides, and diverse transition metal and main group element substrates with complete regeneration of the free borazine Lewis acid. Among the trifluoromethylation products are the principal reagents used for the four major classes of direct trifluoromethylation reactions: trifluoromethyl trimethylsilane ($CF_3$ anion source), $KSO_2CF_3$ ($CF_3$ radical source), Togni I ($CF_3$ cation source), and $CuCF_3$ (cross coupling reagent). Through sequential reagent addition, borazine can be used as a recyclable Lewis acid catalyst. One borazine Lewis acid can be prepared on a kilogram scale from ethanolamine and boric acid and hydrolyzes in water to non-toxic substances, enabling large-scale applications. Using the disclosed methodology, it is now possible to trifluoromethylate diverse substrates using fluoroform and inexpensive bases, enabling a large reduction in the cost of installing the trifluoromethyl group in industrial and laboratory settings. The disclosed strategy of using a fine-tuned borazine Lewis acid to stabilize the trifluoromethyl anion can be applicable to the stabilization of other unstable anions generated using inexpensive bases, and that the stability of the borazine ring to decomposition will enable diverse catalytic applications.

The inert industrial waste gas fluoroform (HCF$_3$) is the most inexpensive source of the medicinally valuable trifluoromethyl functional group, but its weak acidity, strong C—H bond, and unstable CF$_3^-$ anion have prevented practical applications of this reagent from becoming a reality. Of these troublesome properties, the most problematic is the instability of CF$_3^-$ to fluoride elimination, occurring at temperatures as low as −80° C. While certain favorable organic substrates can still be trifluoromethylated in modest yield at such low temperatures, the CF$_3^-$ anion has required stabilization by a strong Lewis acid to enable practical applications beyond the alkylation of simple ketones and aldehydes. Such Lewis-stabilized CF$_3$— adducts have become ubiquitous trifluoromethylation reagents in recent years, providing ready access to nucleophilic, radical, and electrophilic trifluoromethylation reactivity. Despite their popularity, they remain expensive because of the two key dilemmas preventing their economic synthesis from HCF$_3$: the strong base needed to deprotonate HCF$_3$ (pka >28 in DMSO) must be compatible with the strong Lewis acids used to stabilize CF$_3^-$, and the Lewis acid itself must not first abstract a fluoride ion from CF$_3^-$.

To address these dilemmas, expensive, bulky bases such as KHMDS (pKa=30) and P4-tBu (pKa=40) along with low temperatures (−80° C.) have been used to activate HCF$_3$ and generate stable Lewis acid adducts, but only SiR$_3$CF$_3$ (80%), KBF$_3$CF$_3$ (53%), and KSO$_3$CF$_3$ (18%) can be made with this methodology. The only example of HCF$_3$ derived CF$_3$—metal complexes using inexpensive bases is Grushin's "CuCF$_3$" solution, which requires excess base, the toxic solvent DMF, and treatment with hydrofluoric acid. Three other metal complexes can be synthesized through stoichiometric reactions with HCF$_3$, but are impractically expensive: Zn(CF$_3$)$_2$ can be prepared from Zn(TMP)$_2$, Pd(dppp)PhCF$_3$ from the metal hydroxide, and highly unstable Ir(PCP)(H)(CF$_3$) through oxidative addition to the C—H bond; catalytic reactions with these four compounds have not been reported. These strategies have significantly advanced HCF3 activation chemistry and reduced reliance on syntheses using ozone-depleting CF$_3$I to generate CF$_3^-$ reagents such as SiMe$_3$CF$_3$, but the high expense of the required bases, unwanted waste from strong Lewis acids, stoichiometric metals/salts, low temperatures, and low generality have combined to prevent significant reductions in the cost of organic and inorganic trifluoromethylation reactions.

In contrast with current strategies, which employ strong ionic Lewis acids such as TMSCl to stabilize CF$_3^-$, described herein are design neutral, weak Lewis acids that could avoid irreversible reactions with inexpensive, sterically unhindered bases while still providing optimal stabilization to HCF$_3$ derived CF$_3^-$. Importantly, it is hypothesized that a precisely tuned Lewis acidity could provide sufficient stability to CF$_3^-$ to prevent fluoride elimination while still providing high CF$_3^-$ nucleophilicity. These optimized reagents offer the potential for room temperature HCF$_3$ activation, regeneration of the free Lewis acid after high-yielding CF$_3^-$ transfer, and tolerance of cheap, unhindered strong bases, providing superior reactivity and economy while minimizing waste.

SUMMARY

Provided herein is a complex having a structure of formula (I):

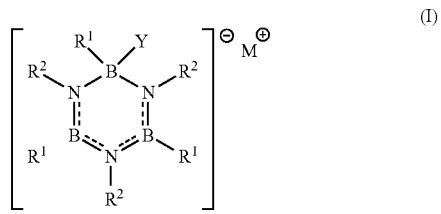

wherein R$^1$ is C$_{1-8}$alkyl, C$_{1-8}$alkoxy, aryl, C$_{3-8}$cycloalkyl, or NR$^3$R$^4$; R$^2$ is C$_{1-8}$alkyl, aryl, or C$_{3-8}$cycloalkyl; or R$^1$ and R$^2$ taken together with the atoms to which they are attached form an optionally substituted 5-7-membered ring; R$^3$ and R$^4$ are each independently H or C$_{1-8}$alkyl, or R$^3$ and R$^4$ taken together with the N forms a 3-5-membered ring; Y is C$_{1-8}$perfluoroalkyl; and M comprises a counterion. In various embodiments, the complex is chiral.

In various embodiments, R$^1$ is NR$^3$R$^4$. In various embodiments, R$^3$ and R$^4$ are each C$_{1-8}$alkyl. In some embodiments, R$^1$ is C$_{1-8}$alkoxy. In some embodiments, R$^1$ is methoxy. In various embodiments, R$^1$ is C$_{1-8}$alkyl. In some embodiments, R$^1$ is methyl. In various embodiments, R$^2$ is C$_{1-4}$alkyl. In various cases, R$^1$ and R$^2$ taken together with the atoms to which they are attached form a 5-6-membered ring. In some cases, R$^1$ and R$^2$ taken together with the atoms to which they are attached form a 5-membered ring. In various cases, the ring is substituted. In some cases, R$^1$ and R$^2$ taken together are —CH$_2$CH$_2$O—. In some cases, R$^1$ is CH$_3$, OCH$_3$, N(CH$_3$)$_2$, or R$^1$ and R$^2$ taken together are —CH$_2$CH$_2$O—.

In various cases, Y comprises one or more $^{18}$F. In various cases, Y is C$_{1-3}$perfluoroalkyl. In some cases, Y is CF$_3$, CHF$_2$, or C$_2$F$_5$. In some cases, Y is CF$_3$. In various embodiments, M comprises Na, K, Rb, Cs, or NH$_4$.

In various cases, the complex further comprises a crown ether. In some cases, the crown ether is 18-crown-6 or 15-crown-5.

In various embodiments, the complex has a structure selected from the group consisting of:

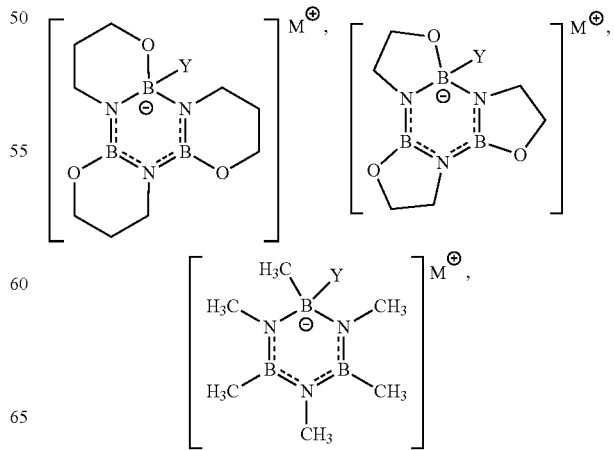

-continued

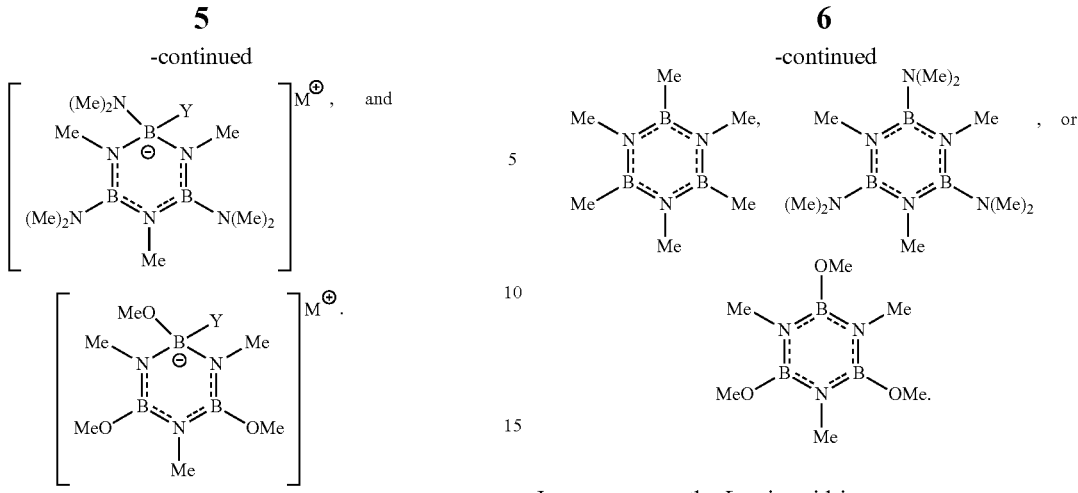

Also provided herein is a method comprising: contacting a base, a Lewis acid, and H—C$_{1-8}$perfluoroalkane to form a complex of the Lewis acid and —C$_{1-8}$perfluoroalkane; wherein the Lewis acid is B(C$_{1-8}$alkoxy)$_3$ or has a structure of formula (II):

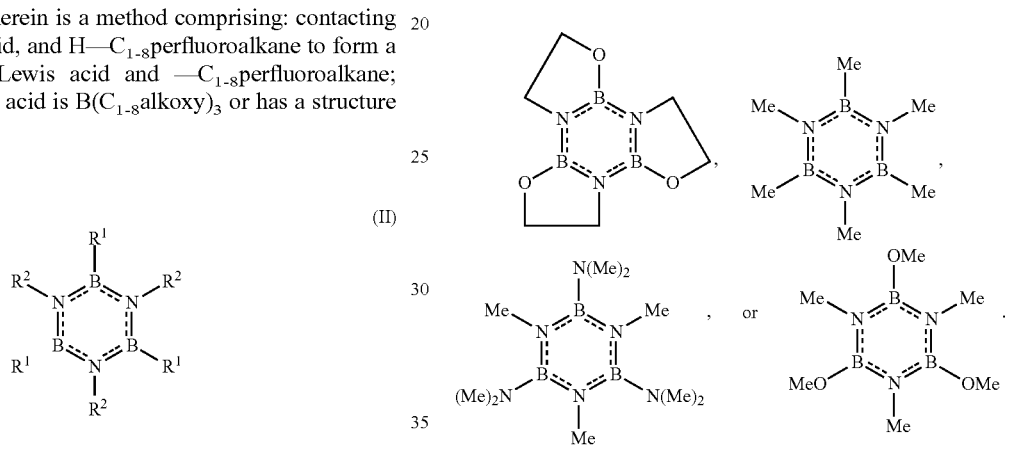

(II)

R$^1$ is C$_{1-8}$alkyl, C$_{1-8}$alkoxy, aryl, C$_{3-8}$cycloalkyl, or NR$^3$R$^4$; R$^2$ is C$_{1-8}$alkyl, aryl, or C$_{3-8}$cycloalkyl; or R$^1$ and R$^2$ taken together with the atoms to which they are attached form a 5-7-membered ring; and R$^3$ and R$^4$ are each independently H or C$_{1-8}$alkyl, or R$^3$ and R$^4$ taken together with the N forms a 3-5 membered ring. In various cases, R$^1$ is NR$^3$R$^4$. In some cases, R$^3$ and R$^4$ are each C$_{1-8}$alkyl. In some cases, R$^1$ is C$_{1-8}$alkoxy. In some cases, R$^1$ is C$_{1-8}$alkyl. In various cases, R$^2$ is C$_{1-4}$alkyl. In some embodiments, R$^1$ and R$^2$ taken together with the atoms to which they are attached form a 5-6-membered ring. In some embodiments, R$^1$ and R$^2$ taken together with the atoms to which they are attached form a 5-membered ring.

In various embodiments, the base is KDMSO, NaDMSO, KOC(CH$_3$)$_3$, KCH$_2$Ph, KH, NaH, or a mixture thereof. In some embodiments, the base comprises KDMSO. In some embodiments, the base comprises NaDMSO.

In various cases, the Lewis acid is

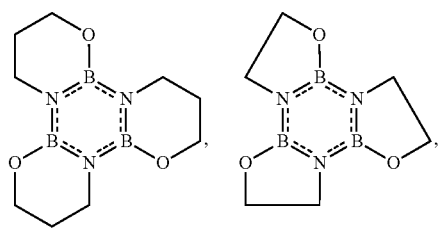

In some cases, the Lewis acid is

[structures shown]

In some cases, the Lewis acid is

[structure shown]

In some cases, the Lewis acid is B(OMe)$_3$.

In various embodiments, the method further comprises perfluoroalkylating an aromatic or heteroaromatic compound by admixing the complex of any one of claims 1 to 20 or [B(C$_{1-8}$perfluoroalkyl)(C$_{1-8}$alkoxy)$_3$]$^-$ with the aromatic or heteroaromatic compound to form a perfluoroalkylaromatic or perfluoroalkylheteroaromatic compound.

In various cases, the method further comprises perfluoroalkylating an aromatic or heteroaromatic compound by admixing the complex of any one of claims 1 to 20 or [B(C$_{1-8}$perfluoroalkyl)(C$_{1-8}$alkoxy)$_3$]$^-$ with the aromatic or heteroaromatic compound to form a perfluoroalkylated aromatic or heteroaromatic anionic intermediate. In some cases, the method further comprises oxidizing the perfluoroalkylated aromatic or heteroaromatic anionic intermediate to form a perfluoroalkylaromatic or perfluoroheteraromatic compound. In some cases, the method further comprises admixing the perfluoroalkylated aromatic or heteroaromatic anionic intermediate and an electrophile to form a dearomatized product substituted with (i) a substituent from the electrophile and (ii) a perfluoroalkyl group.

In various embodiments, the aromatic or heteroaromatic compound is activated by a Lewis acid. In some embodiments, the heteroaromatic compound comprises a pyridine, quinoline, pyrimidine, or triazine ring. In various embodiments, the Lewis acid is regenerated.

In various cases, the method further comprises reacting the complex with a reagent to form a perfluoroalkylating reagent and regenerate the Lewis acid. In various cases, the method further comprises isolating the regenerated Lewis acid. In some cases, the isolating comprises extraction. In some cases, the isolating comprises distillation.

In various embodiments, the reagent is selected from the group consisting of P(Ar)$_2$L, Pd(TMEDA)(Ar)L, ZnL$_2$, Zn(TMEDA)L$_2$, Bi(L)$_3$, Ph$_2$S$_2$, Ph$_2$Se$_2$, LCN, CO$_2$, CuL, AgL, SnMe$_3$L, PbMe$_3$L, Au(iPr)L, S$_8$, trialkylsilyl-L, SO$_2$, an iodonium(III) reagent, Te, and Se; each L independently is Cl, Br, I, NO$_3$, OSO$_2$Ar, or OSO$_2$CF$_3$; and Ar is aryl. In some embodiments, the iodonium reagent is

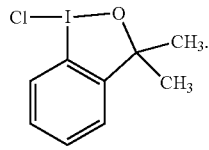

In some embodiments, the perfluoroalkylating reagent is

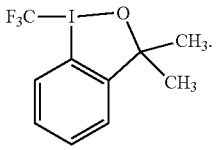

In various embodiments, the perfluoroalkylating reagent is P(Ar)$_2$CF$_3$, Zn(CF$_3$)$_2$, Pd(TMEDA)(Tol)CF3, CuCF$_3$, AgCF$_3$, SnMe$_3$CF$_3$, SiMe$_3$CF$_3$, PbMe$_3$CF$_3$, Au(iPr)CF$_3$, Zn(TMEDA)(CF$_3$)$_2$, Bi(CF$_3$)$_2$Cl, PhSCF$_3$, PhSeCF$_3$, BrCF$_3$, CO$_2$CF$_3^-$, SO$_2$CF$_3^-$, SCF$_3^-$, TeCF$_3^-$, or SeCF$_3^-$.

In various cases, the contacting or reacting occurs in a polar, aprotic solvent. In some cases, the polar, aprotic solvent comprises DMSO. In some cases, the polar, aprotic solvent comprises THF. In some cases, the polar, aprotic solvent comprises an ether.

In various embodiments, the contacting and/or reacting is at a temperature of −10 to 30° C. In some embodiments, the temperature is 20-25° C.

In various cases, the HC$_{1-8}$ perfluoroalkane is HC$_{1-3}$perfluoroalkane. In some cases, the HC$_{1-8}$ perfluororalkane is fluoroform. In some cases, the HC$_{1-8}$ perfluororalkane is difluoromethane. In various cases, the HC$_{1-8}$ perfluoroalkane comprises one or more $^{18}$F.

In various embodiments, the method further comprises perfluoroalkylating an aromatic or heteroaromatic compound by admixing a perfluoroalkylating reagent described herein with the aromatic or heteroaromatic compound to form a perfluoroalkylaromatic or perfluoroalkylheteroaromatic compound.

In various embodiments, the aromatic or heteroaromatic compound is an NO$_2$- or Cl-substituted aromatic compound (Ar—NO$_2$ or Ar—Cl) or NO$_2$- or Cl-substituted heteroaromatic compound (Het-NO$_2$ or Het-Cl) which is then substituted for the perfluoroalkyl group to form Ar-perfluoroalkyl or Het-perfluoroalkyl.

In various embodiments, the Ar—Cl or Het-Cl, at the chloro carbon, is disubstituted with the perfluoroalkylating reagent as shown in the scheme below

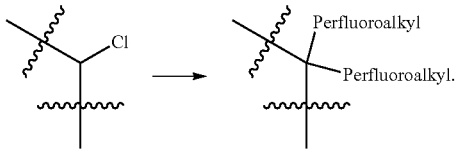

In various embodiments, the method further comprises perfluoroalkylating a carbonyl or imine compound by admixing the complex of any one of claims 1 to 20 or the perfluoroalkylating reagent of claim 44 or 45 with the carbonyl or imine compound to form a perfluoroalkylated alcohol or perfluoroalkylated amine as shown in the scheme below:

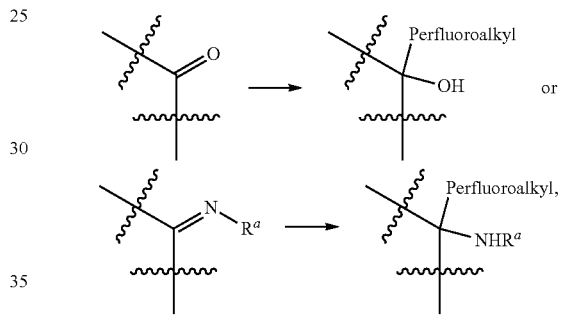

and R$^a$ is H or a C$_{1-8}$alkyl. In some embodiments, R$^a$ is H. In various embodiments, R$^a$ is C$_{1-8}$alkyl.

In various cases, the carbonyl compound is an aldehyde. In various cases, the carbonyl compound is a ketone. In some cases, the carbonyl compound is an isocyanate or isothiocyanate. In some cases, the carbonyl compound is an acid chloride. In various cases, the carbonyl compound is a carbonate. In various cases, the carbonyl compound is an acid anhydride. In various cases, the carbonyl compound is an ester.

DETAILED DESCRIPTION

Disclosed herein are borazine complexes (which are alternatively referred to as compounds) containing a perfluoroalkyl anion and methods of using the same in perfluoroalkylation reactions.

Figure 1A:
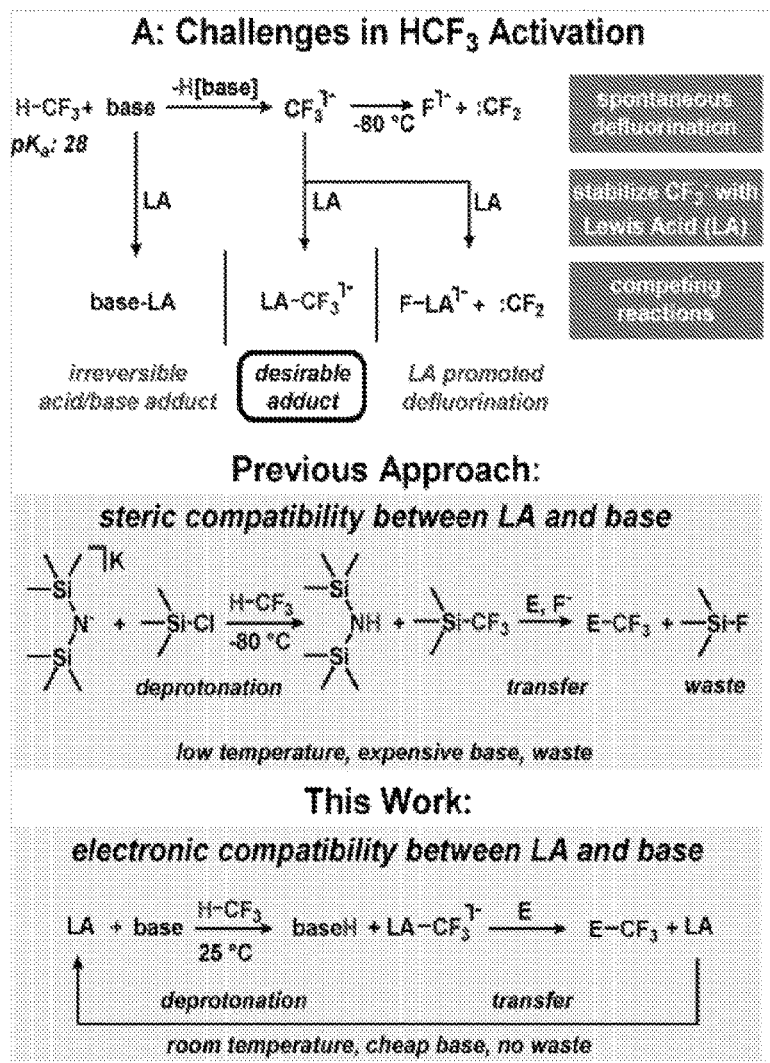
FIG. 1A shows challenges and solutions associated with HCF$_3$ activation (E=electrophile).

A challenge for the economic synthesis of LA-CF$_3^-$ reagents from HCF$_3$ is poor compatibility between components of the reaction mixture. The Lewis acid and Brønsted base must coexist in solution prior to HCF$_3$ addition because the CF$_3^-$ anion is unstable. Furthermore, the strong base needed to deprotonate HCF$_3$ (pKa >28 in DMSO) cannot irreversibly react with the Lewis acid, and the Lewis acid itself must not promote CF$_3^-$ defluorination (FIG. 1A). In the last decade, two primary strategies have emerged to provide compatible pairs of Lewis acids and bases: the use of steric bulk to separate reactive Lewis acidic and basic centers (steric control), and the use of Lewis pairs with mismatched strength between Lewis acidic and basic centers to enable reversible adduct formation (electronic control). Recently, steric control has been used to activate HCF$_3$ in a stepwise mechanism using a mixture of very bulky bases (potassium bis(trimethylsilyl)amide (KHMDS) and phosphazene superbases) and Lewis acids such as SiMe$_3$Cl. However, this strategy is inherently limited by the high expense of the required bases, cryogenic temperatures, and low generality. Additionally, the instability of the CF$_3^-$ intermediate requires the combination of KHMDS and electrophiles prior to addition of HCF$_3$, leading to undesired competing pathways that limit the scope of this reaction to simple electrophiles.

In contrast with the use of steric bulk at the base, provided herein is a system for HCF$_3$ activation using neutral, weak Lewis acids to avoid irreversible reactions with cheap bases and provide optimal stabilization of CF$_3^-$ (FIG. 1A). While not being bound by theory, it was hypothesized that a precisely tuned Lewis acid could be readily recyclable, impart Grignard-like CF$_3^-$ nucleophilicity to a LA-CF$_3$ adduct, and prevent fluoride elimination from CF$_3^-$ at room temperature. This represents a distinct concept in fluoroform activation: no systematic approach for the selection of Lewis acids capable of providing these three desirable properties has been reported.

Figure 1B:
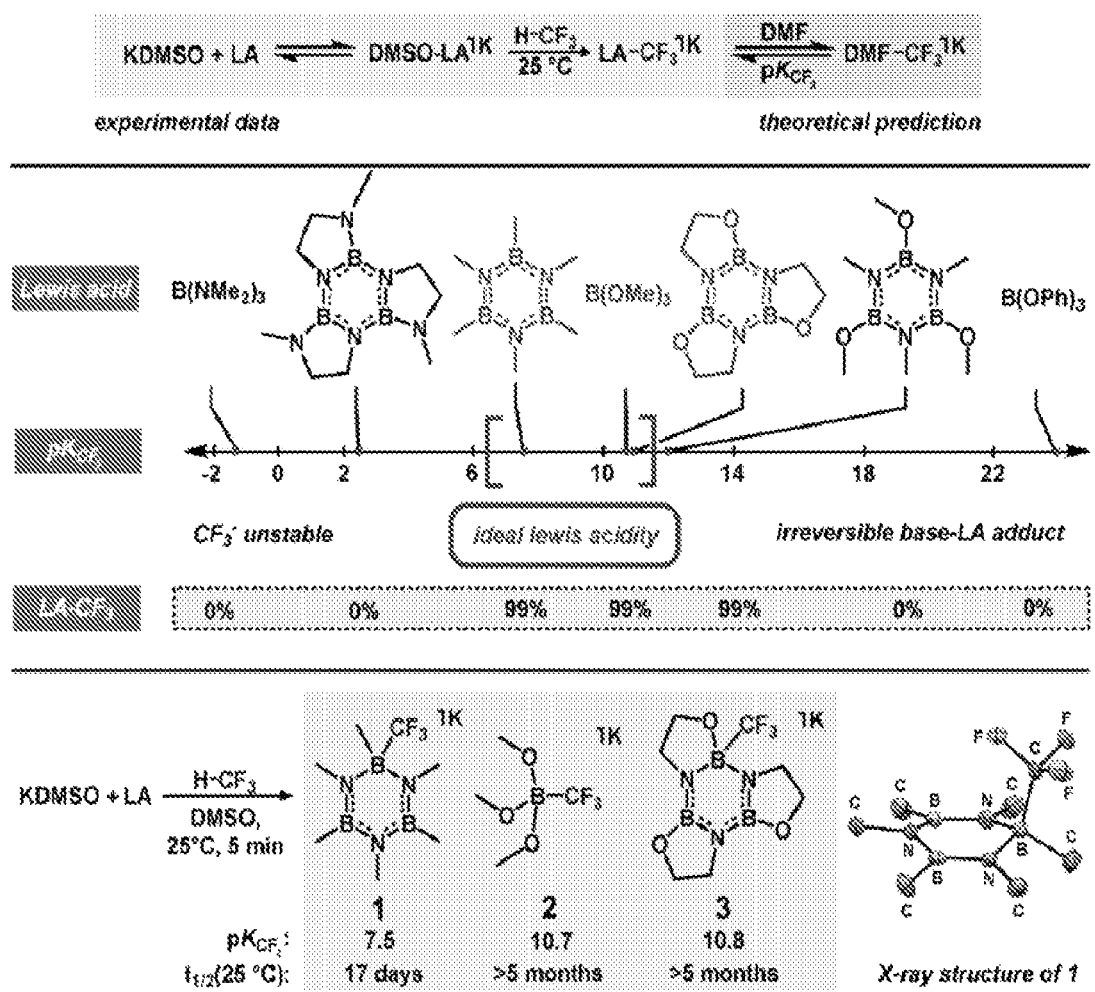
FIG. 1B shows the rational selection of Lewis acids for HCF$_3$ activation through a complementary theoretical/experimental approach. pK$_{CF_3}$=log$_{10}$(K) for the binding affinity of a given Lewis acid for CF$_3$— as compared to DMF (pK$_{CF_3}$(DMF)=0).

Low-cost alkali metal hydride derived bases (NaH: $0.10/mole, KH: $35/mole) were used for HCF$_3$ deprotonation, along with boron-based Lewis acids. This class of Lewis acids has a wide range of Lewis acidities and high natural abundance. A widely used solvent, dimethylsulfoxide (DMSO), reacts with alkali hydrides to produce the highly reactive dimsyl anion (DMSO$^-$, pKa=35). The CF$_3^-$ affinity of a variety of boron Lewis acids was assessed computationally and tabulated in the form of pKCF$_3$ values as a unified scale of CF$_3^-$ affinity. These data were used to select a set of Lewis acids representing a 20 pKCF$_3$ span for experimental evaluation: [DMSO]$^-$ and each Lewis acid were combined at room temperature, HCF$_3$ gas was added (1 atm), and the reaction was assessed by $^{19}$F NMR spectroscopy. Lewis acids with pKCF$_3$ values above 11 exhibited irreversible coordination to [DMSO]$^-$, and did not react with HCF3. Conversely, Lewis acids with pKCF$_3$ values below 6 were insufficiently Lewis acidic to stabilize the CF$_3^-$ anion resulting from HCF$_3$ deprotonation, leading to immediate decomposition (FIG. 1B). As such, Lewis acids having a pKCF$_3$ value between 6 and 11 are specifically contemplated.

Certain of the complexes as disclosed herein may exist as stereoisomers (i.e., isomers that differ only in the spatial arrangement of atoms) including optical isomers and conformational isomers (or conformers). The complexes disclosed herein include all stereoisomers, both as pure individual stereoisomer preparations and enriched preparations of each, and both the racemic mixtures of such stereoisomers as well as the individual diastereomers and enantiomers that may be separated according to methods that are known to those skilled in the art. Additionally, the complexes disclosed herein include all tautomeric forms of the compounds.

Definitions

As used herein, the term "alkyl" refers to straight chained and branched hydrocarbon groups, including but not limited to, methyl, ethyl, n-propyl, i-propyl, n-butyl, sec-butyl, t-butyl, n-pentyl, 2-methylbutyl, 3-methylbutyl, 2,2-dimethylpropyl, n-hexyl, 2-methylpentyl, 3-methylpentyl, 4-methylpentyl, 2,2-dimethylbutyl, 2,3-dimethylbutyl, 3,3-dimethylbutyl, and 2-ethybutyl. The term C$_{m-n}$ means the alkyl group has "m" to "n" carbon atoms. The term "alkylene" refers to an alkyl group having a substituent. An alkyl (e.g., methyl), or alkylene (e.g., —CH$_2$—), group can be substituted with one or more, and typically one to three, of independently selected halo, trifluoromethyl, trifluoromethoxy, hydroxy, alkoxy, nitro, cyano, alkylamino, or amino groups, for example.

The term "alkoxy" is defined as —OR, wherein R is alkyl.

The term "perfluoroalkyl" is an alkyl group that has all or most (e.g., at least 65%) of the hydrogen atoms substituted with fluorine atoms. The term C$_{m-n}$ means the perfluoroalkyl group has "m" to "n" carbon atoms. In some cases, the perfluoroalkyl has 1 to 8, or 1 to 6 carbon atoms. In cases where a perfluoroalkyl group has a hydrogen atom, that hydrogen atom can be specified, such as, for example HC$_{1-8}$perfluoroalkane. Some specific examples of perfluoroalkyl groups contemplated include, but are not limited to, CF$_3$, CHF$_2$, CF$_2$CF$_3$, perfluoropropyl, perfluorobutyl, and perfluorohexyl.

As used herein, the term "counterion" refers to an ion associated with a charged species to maintain charge neutrality. Borazine compounds disclosed herein are negatively charged, and as such, have a positively charged counterion associated therewith. Examples of positively charged counterions include H$^+$, Li$^+$, Na$^+$, K$^+$, Rb$^+$, Cs$^+$, Mg$^{2+}$, and Ca$^{2+}$.

As used herein, the term "aryl" refers to 5-, 6-, or 7-membered substituted or unsubstituted single-ring aromatic groups in which each atom of the ring is carbon, or to a polycyclic ring system having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Specific aryl groups contemplated include, but are not limited to, benzene, naphthalene, phenanthrene, phenol, and aniline.

As used herein, the term "cycloalkyl" refers to a monocyclic or polycyclic (e.g., bicyclic), saturated or partially unsaturated, ring system containing three or more (e.g., three to twelve or three to eight) carbon atoms. Specifically contamplated examples include, but are not limited to, cyclopropyl, cyclobutyl, cyclopentyl, cyclohexyl, cycloheptyl, and cyclooctyl. In some cases, the cycloalkyl is substituted.

As used herein, the term "anionic" refers to any moiety or group bearing a negative charge.

As used herein, the term "electrophile" refers to a compound which are capable of reacting with a perfluoroalkylated anion, e.g., via an addition, substitution, or protonation reaction. Contemplated electrophiles include, but are not limited to, $Cl_2$, $Br_2$, $I_2$, $H_2O$, alkyl-OH, aromatic or α,β-unsaturated aldehydes and ketones, carbon dioxide, alkyl halides, and Lewis acids.

The term "substituted," refers to moieties having substituents replacing a hydrogen on one or more non-hydrogen atoms of a specific moiety on a compound. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. Substituents can include, for example, an alkyl, alkenyl, alkynyl, a halogen, a hydroxyl, a carbonyl (such as a carboxyl, an ester, a thioester, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a carbocyclyl (e.g., cycloalkyl, cycloalkenyl), a heterocyclyl (e.g., heterocycloalkyl), an aralkyl, a heteroaralkyl, or an aromatic (i.e., aryl) or heteroaromatic (i.e., heteroaryl) moiety. It will be understood by those skilled in the art that the moieties substituted on the hydrocarbon chain can themselves be substituted, if appropriate. In some embodiments, the substituent is a halogen, such as fluorine. When a chemical functional group includes more than one substituent, the substituents can be bound to the same carbon atom or to two or more different carbon atoms. A substituted chemical functional group can itself include one or more substituents.

The term "TMEDA" refers to tetramethylethylenediamine.

Complexes of Formula (I)

In one aspect, the disclosure provides a complex having a structure of formula (I):

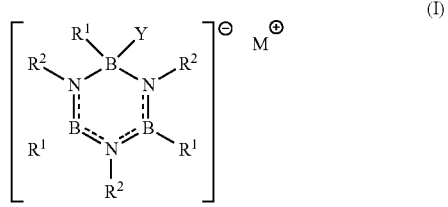

(I)

wherein $R^1$ is $C_{1-8}$alkyl, $C_{1-8}$alkoxy, aryl, $C_{3-8}$cycloalkyl, or $NR^3R^4$; $R^2$ is $C_{1-8}$alkyl, aryl, or $C_{3-8}$cycloalkyl; or $R^1$ and $R^2$ taken together with the atoms to which they are attached form an optionally substituted 5-7-membered ring; $R^3$ and $R^4$ are each independently H or $C_{1-8}$alkyl, or $R^3$ and $R^4$ taken together with the N forms a 3-5-membered ring; Y is $C_{1-8}$perfluoroalkyl; and M is a counterion.

In some embodiments, $R^1$ is $NR^3R^4$. In some embodiments, $R^3$ and $R^4$ are each $C_{1-8}$alkyl. In some embodiments, $R^1$ is $C_{1-8}$alkoxy. In some embodiments, $R^1$ is methoxy. In some embodiments, $R^1$ is $C_{1-8}$alkyl. For example, $R^1$ is methyl, ethyl, or propyl. In some embodiments, $R^1$ is $CH_3$, $OCH_3$, $N(CH_3)_2$, or $R^1$ and $R^2$ taken together are $-CH_2CH_2O-$.

In various embodiments, $R^2$ is $C_{1-4}$alkyl. In some embodiments, $R^1$ and $R^2$ taken together with the atoms to which they are attached form a 5-6-membered ring. In some embodiments, $R^1$ and $R^2$ taken together with the atoms to which they are attached form a 5-membered ring. In some cases, the ring is substituted. In some embodiments, $R^1$ and $R^2$ taken together are $-CH_2CH_2O-$.

The complexes disclosed herein can also be chiral.

In various embodiments, Y comprises one or more $^{18}F$ atoms. In some embodiments, Y is $C_{1-3}$perfluoroalkyl. For example, Y can be $CF_3$, $CHF_2$, or $C_2F_5$. In some cases, Y is $CF_3$.

In some embodiments, M comprises Na, K, Rb, Cs, or $NH_4$.

The complexes disclosed herein can also comprise a crown ether. In some cases, the crown ether is 18-crown-6 or 15-crown-5.

For example, the complex can have a structure selected from the group consisting of:

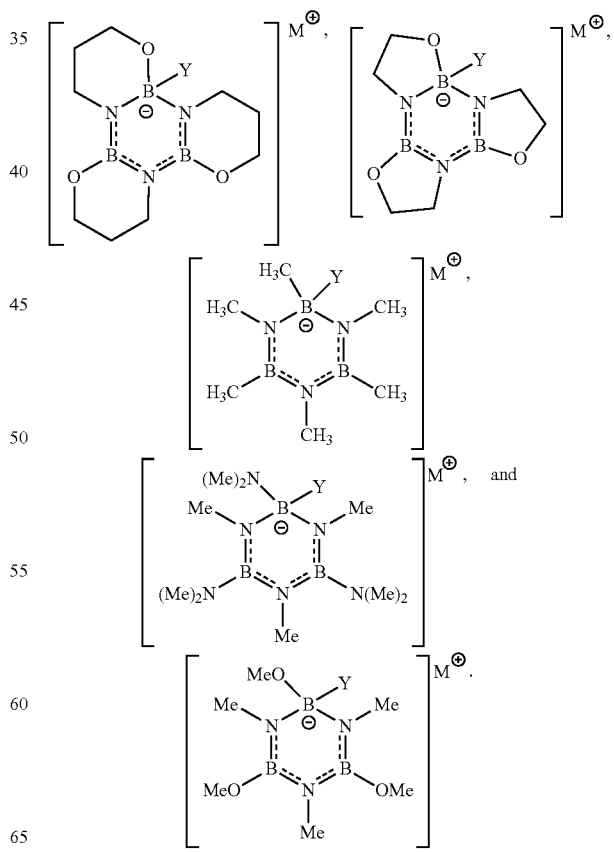

Method of Using Compounds Disclosed Herein

In one aspect, the disclosure provides a method comprising: contacting a base, a Lewis acid, and H—C$_{1-8}$perfluoroalkane to form a complex of the Lewis acid and a C$_{1-8}$perfluoroalkyl; wherein the Lewis acid is B(C$_{1-8}$alkoxy)$_3$ or has a structure of formula (II):

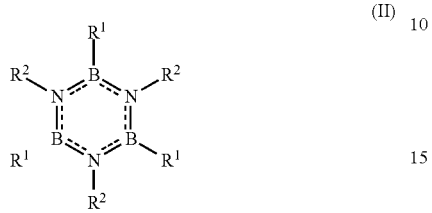

(II)

R$^1$ is C$_{1-8}$alkyl, C$_{1-8}$alkoxy, aryl, C$_{3-8}$cycloalkyl, or NR$^3$R$^4$; R$^2$ is C$_{1-8}$alkyl, aryl, or C$_{3-8}$cycloalkyl; or R$^1$ and R$^2$ taken together with the atoms to which they are attached form a 5-7-membered ring; R$^3$ and R$^4$ are each independently H or C$_{1-8}$alkyl, or R$^3$ and R$^4$ taken together with the N forms a 3-5 membered ring.

In various embodiments, the contacting or reacting occurs in a polar, aprotic solvent. In some cases, the polar, aprotic solvent comprises DMSO. In some cases, the polar, aprotic solvent comprises THF. In some embodiments, the polar, aprotic solvent comprises an ether. In various embodiments, the contacting and/or reacting is at a temperature of −10 to 30° C. For example, the temperature is 20-25° C.

Suitable bases include, but are not limited to, KDMSO, NaDMSO, KOC(CH$_3$)$_3$, KCH$_2$Ph, KH, NaH, or a mixture thereof. In some cases, the base comprises KDMSO. In other cases, the base comprises NaDMSO.

In various embodiments, the HC$_{1-8}$ perfluoroalkane is HC$_{1-3}$perfluoroalkane. For example, the HC$_{1-8}$ perfluororalkane can be fluoroform (HCF$_3$), H$_2$CF$_2$, HCF$_2$CF$_3$, or HCF$_2$CF$_2$CF$_3$. In some cases, the HC$_{1-8}$ perfluoroalkane comprises one or more $^{18}$F atoms.

In some embodiments, R$^1$ is NR$^3$R$^4$. In some of these cases, R$^3$ and R$^4$ are each C$_{1-8}$alkyl. For example, R$^3$ and R$^4$ can each independently be methyl, ethyl, propyl, or butyl. In various embodiments, R$^1$ is C$_{1-8}$alkoxy (e.g., methoxy, ethoxy, or propoxy). In some embodiments, R$^1$ is C$_{1-8}$alkyl. For example, R$^1$ can be methyl, ethyl, propyl, or butyl.

In various embodiments, R$^2$ is C$_{1-4}$alkyl. For example, R$^2$ can be methyl, ethyl, propyl, or butyl.

In some embodiments, R$^1$ and R$^2$ taken together with the atoms to which they are attached form a 5-6-membered ring. For example, R$^1$ and R$^2$ taken together with the atoms to which they are attached form a 5-membered ring.

In various embodiments, the Lewis acid is

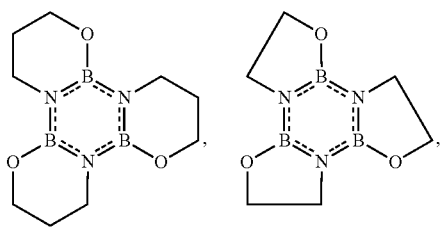

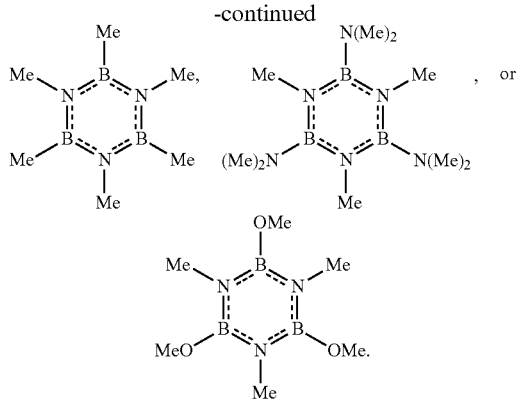

For example, the Lewis acid is

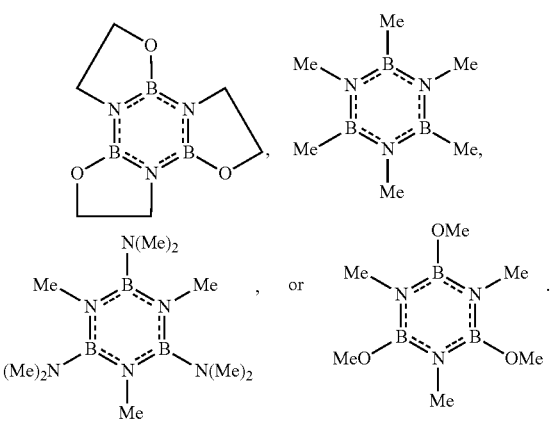

In some cases, the Lewis acid is

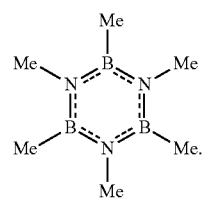

In other cases, the Lewis acid is B(OMe)$_3$.

The method can further comprise perfluoroalkylating an aromatic or heteroaromatic compound by admixing a complex described herein or [B(C$_{1-8}$perfluoroalkyl)(C$_{1-8}$alkoxy)$_3$]$^-$ with the aromatic or heteroaromatic compound to form a perfluoroalkylaromatic or perfluoroalkylheteroaromatic compound.

The method can further comprise perfluoroalkylating the C—H bond in an aromatic or heteroaromatic compound, including but not limited to pyridine, quinoline, pyrimidine, or triazine-containing compounds, which may or may not be activated by a Lewis acid, to form anionic intermediates that may either be oxidized to perfluoroalkylated arenes or further functionalized with electrophilic species such as benzyl bromide to produce dearomatized products, by admixing a complex described herein or [B(C$_{1-8}$perfluoroalkyl)(C$_{1-8}$alkoxy)$_3$]$^-$ with the aromatic or heteroaromatic compound to form a perfluoroalkyl compound.

The method can further comprise regenerating the Lewis acid. In various cases, the regenerated Lewis acid is isolated. In some cases, the isolating comprises extraction. In other cases, the isolating comprises distillation.

The method can further comprise reacting the complex with a reagent to form a perfluoroalkylating reagent and regenerate the Lewis acid. Suitable reagents include, but are not limited to, P(Ar)$_2$L, Pd(TMEDA)(Ar)L, ZnL$_2$, Zn(TMEDA)L$_2$, Bi(CF$_3$)$_2$Cl, Ph$_2$S$_2$, Ph$_2$Se$_2$, LCN, CO$_2$, CuL, AgL, SnMe$_3$L, PbMe$_3$L, Au(iPr)L, S$_8$, trialkylsilyl-L, SO$_2$, an iodonium(III) reagent, Te, and Se; each L independently is Cl, Br, I, NO$_3$, OSO$_2$Ar, or OSO$_2$CF$_3$; and Ar is aryl. For example, the iodonium reagent can be

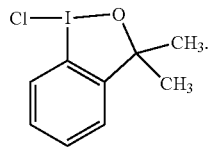

In some embodiments, the perfluoroalkylating reagent is

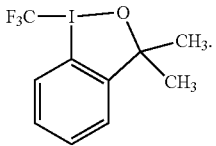

In various embodiments, the perfluoroalkylating reagent is P(Ar)$_2$CF$_3$, Zn(CF$_3$)$_2$, Pd(TMEDA)(Tol)CF3, CuCF$_3$, AgCF$_3$, SnMe$_3$CF$_3$, SiMe$_3$CF$_3$, PbMe$_3$CF$_3$, Au(iPr)CF$_3$, Zn(TMEDA)(CF$_3$)$_2$, BiCl$_3$, PhSCF$_3$, PhSeCF$_3$, BrCF$_3$, CO$_2$CF$_3$$^-$, SO$_2$CF$_3$$^-$, SCF$_3$$^-$, TeCF$_3$$^-$, or SeCF$_3$$^-$. The method can further comprise perfluoroalkylating an aromatic or heteroaromatic compound by admixing the perfluoroalkylating reagent as disclosed herein with the aromatic or heteroaromatic compound to form a perfluoroalkylaromatic or perfluoroalkylheteroaromatic compound.

In various embodiments, the aromatic or heteroaromatic compound is an NO$_2$- or Cl-substituted aromatic compound (Ar—NO$_2$ or Ar—Cl) or NO$_2$- or Cl-substituted heteroaromatic compound (Het-NO$_2$ or Het-Cl) which is then substituted for the perfluoroalkyl group to form Ar-perfluoroalkyl or Het-perfluoroalkyl. In some cases, the Ar—Cl or Het-Cl, at the chloro carbon, is disubstituted with the perfluoroalkylating reagent, breaking aromaticity of the aryl or heteroaryl compound, as shown in the scheme below

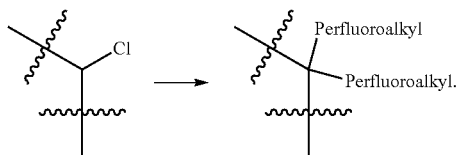

The method can further comprise perfluoroalkylating a carbonyl or imine compound by admixing a complex or a perfluoroalkylating reagent disclosed herein with the carbonyl or imine compound to form a perfluoroalkylated alcohol or perfluoroalkylated amine as shown in the scheme below:

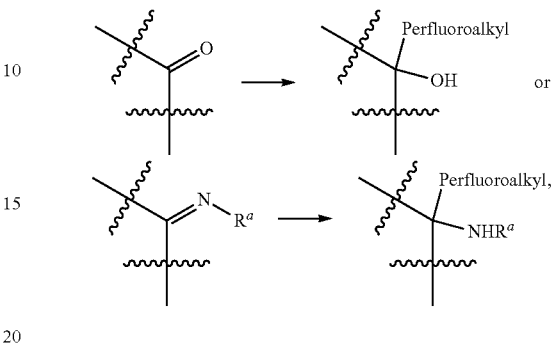

and $R^a$ is H or a $C_{1-8}$alkyl. Suitable carbonyl compounds include, but are not limited to, aldehydes, ketones, isocyanates, isothiocyanates, acid chlorides, carbonates, acid anhydrides, and esters. In some embodiments, $R^a$ is H. In some embodiments, $R^a$ is $C_{1-8}$alkyl, e.g., methyl, ethyl, butyl, or octyl.

Use of Compounds Disclosed Herein to Synthesize Perfluoroalkylating Agents

The complexes disclosed herein can be used in a variety of chemical transformations to introduce one or more perfluoroalkyl groups to a reagent. For example, the complexes can be transmetalated with various Lewis acids (e.g., TMSCl, CuI, ZnCl$_2$) to form metalated perfluoroalkyl nucleophiles (e.g., TMSCF$_3$, CuCF$_3$, Zn(CF$_3$)$_2$). The complexes can also react with heteroatom-centered electrophiles (e.g., S$_8$, Ph$_2$S$_2$) to form heteroatom-substituted perfluoroalkanes (e.g., KSCF$_3$, PhSCF$_3$).

For example, three Lewis acids showed both reversible KDMSO coordination and deprotonation of HCF$_3$ to produce room temperature stable LA-CF$_3$ adducts, K(B$_3$N$_3$Me$_6$)CF$_3$ (1), K(B(OMe)$_3$)CF$_3$ (2), and K(BOC$_2$H$_4$N)$_3$CF$_3$ (3), in greater than 95% yield. These Lewis acids are extremely inexpensive; B(OMe)$_3$ is a commodity chemical (<$1/mole), and B$_3$N$_3$Me$_6$ and (BOC$_2$H$_4$N)$_3$ can be synthesized from cheap, simple starting materials. Worth noting is that 2 is a commonly used but currently expensive CF$_3$$^-$ reagent with many reported applications. Solutions of 1 and 3 are oxygen-stable, decompose on exposure to moisture, and their thermal decomposition returns the free Lewis acid. Solutions of 1 were also prepared in tetrahydrofuran (THF) by combining benzyl potassium, B$_3$N$_3$Me$_6$, 18-crown-6, and HCF$_3$ in THF at 0° C. for five minutes; from this solution, 1 was obtained as a weighable solid in 95% yield and was structurally characterized by X-ray crystallography.

Figure 2:
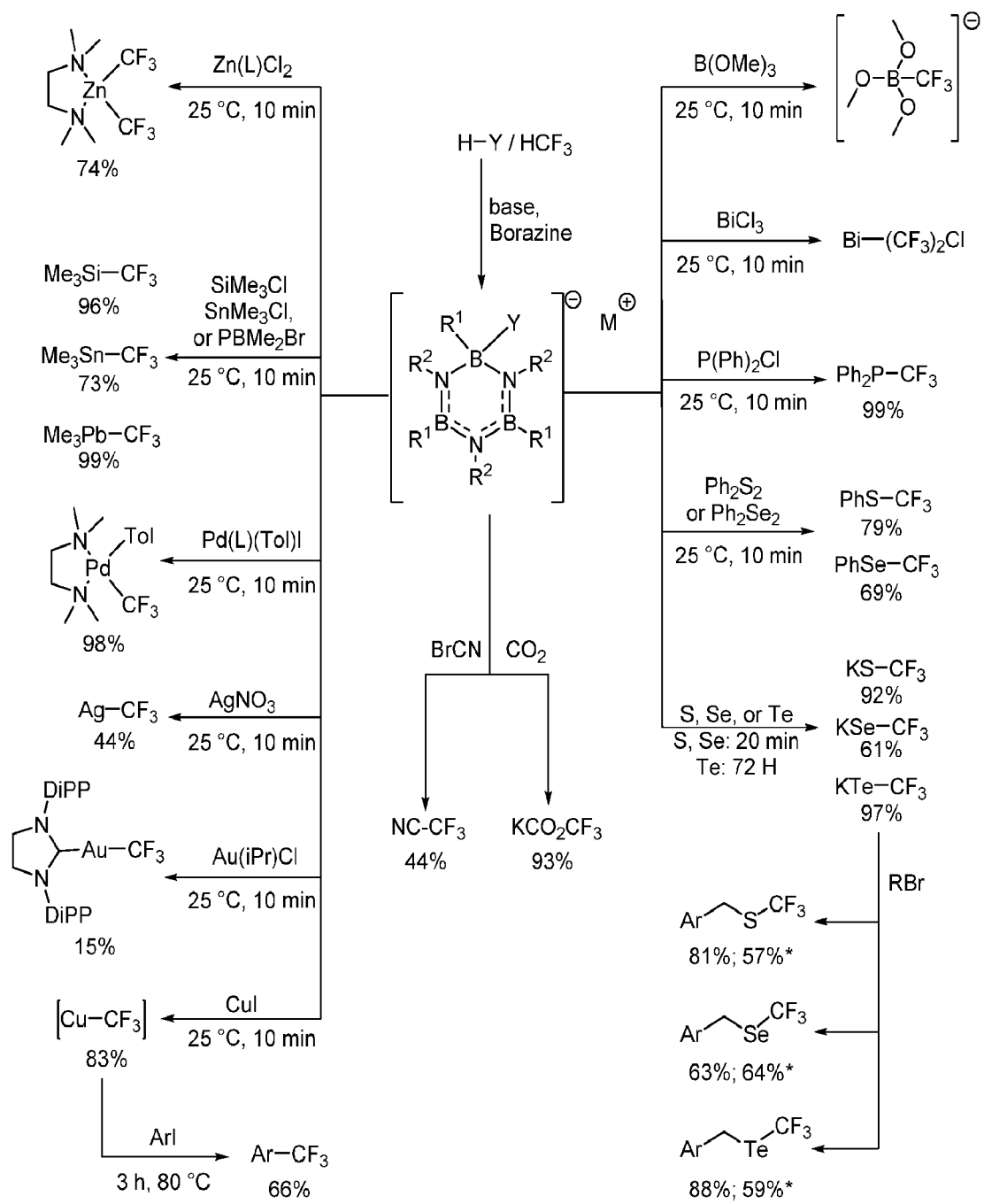
FIG. 2 shows inorganic trifluoromethylation reactions using complex 1 with a variety of electrophiles.

The isolated adduct 1 is a highly reactive source of nucleophilic CF$_3$$^-$, and reacts cleanly with a wide variety of organic and inorganic electrophiles at room temperature (FIG. 2). Generation of metal-CF$_3$ complexes from HCF$_3$ has historically required excess base, toxic solvents such as dimethylformamide, and/or stabilization with Brønsted acids. Much like a Grignard reagent, 1 cleanly transfers CF$_3$$^-$ to metal complexes such as Pd(TMEDA)(Tol)I, AgNO$_3$, CuI, SnMe$_3$Cl, PbMe$_3$Br, Au(iPr)Cl, and Zn(TMEDA)Cl$_2$ to generate Pd(TMEDA)(Tol)CF3, CuCF3, SnMe$_3$CF$_3$, AgCF$_3$, PbMe$_3$CF$_3$, Au(iPr)CF$_3$, and Zn(TMEDA)(CF$_3$)$_2$ within 10 minutes; the CuCF$_3$ solution can be directly used in a cross-coupling reaction to provide trifluoromethylbiphenyl in high yield. 1 also reacts with many inorganic main-group compounds. In agreement with the calculated p$K_{CF_3}$ values, 1 transfers $CF_3^-$ to $B(OMe)_3$ in high yield to afford 2. Nucleophilic reactions also proceed with $PPh_2Cl$, $BiCl_3$, BrCN, and $CO_2$ to afford $PPh_2CF_3$, $Bi(CF_3)_2Cl$, $CF_3Br$, and $KCO_2CF_3$ in excellent yield. Metal-catalyzed trifluoromethylation reactions are often limited by currently available LA-$CF_3$ reagents, which are either insufficiently strong $CF_3^-$ nucleophiles or undergo unproductive side reactions with competing nucleophiles and electrophiles. With few exceptions, the performance of 1 in inorganic trifluoromethylations far exceeds that of previously reported $CF_3^-$ reagents ($KB(OMe)_3CF_3$, $SiMe_3CF_3/KF$) and $HCF_3$ activation methodologies ($KOtBu/DMF/HCF_3$, $KHMDS/HCF_3$) because it lacks competing —O, —N, and —F nucleophilic sites.

Use of Compounds Disclosed Herein as Perfluoroalkylating Agents

Inorganic Reactions:

The disclosed complexes can be used in chemical reactions on inorganic starting material. For example, elemental sulfur, selenium, and tellurium are inexpensive and attractive targets for nucleophilic trifluoromethylation. The —$SCF_3$ and —$SeCF_3$ functional groups are more lipophilic than $CF_3$ itself, and have become increasingly important in medicinal chemistry. Recently, the synthesis of $SCF_3^-$ was attempted from $HCF_3$ and elemental sulfur using a $HCF_3$/KHMDS system at −80° C., but only partially reacted [$SnCF_3$]$^-$ oligomers were obtained in 18% yield. It was hypothesized that the stability and high nucleophilicity of 1 would allow a higher reaction temperature in which $S_8$, Se, and Te are more soluble and can be completely consumed to produce $SCF_3^-$, $SeCF_3^-$, and $TeCF_3^-$ rather than partially reacted oligomers. Indeed, 1 reacts cleanly with elemental sulfur, selenium, and tellurium to produce $SCF_3^-$, $SeCF_3^-$, and $TeCF_3^-$ at room temperature; these anions can undergo subsequent one pot alkylation with a benzyl bromide in 87%, 68%, and 60% isolated yields (FIG. 2), respectively. Additionally, disulfides and diselenides react cleanly with 1, generating trifluoromethyl thio- and seleno-ethers in good yield. Previously inaccessible inorganic main group congeners can be accessed using the disclosed complexes and methods, including trifluoromethyltellurium ethers.

Figure 3:
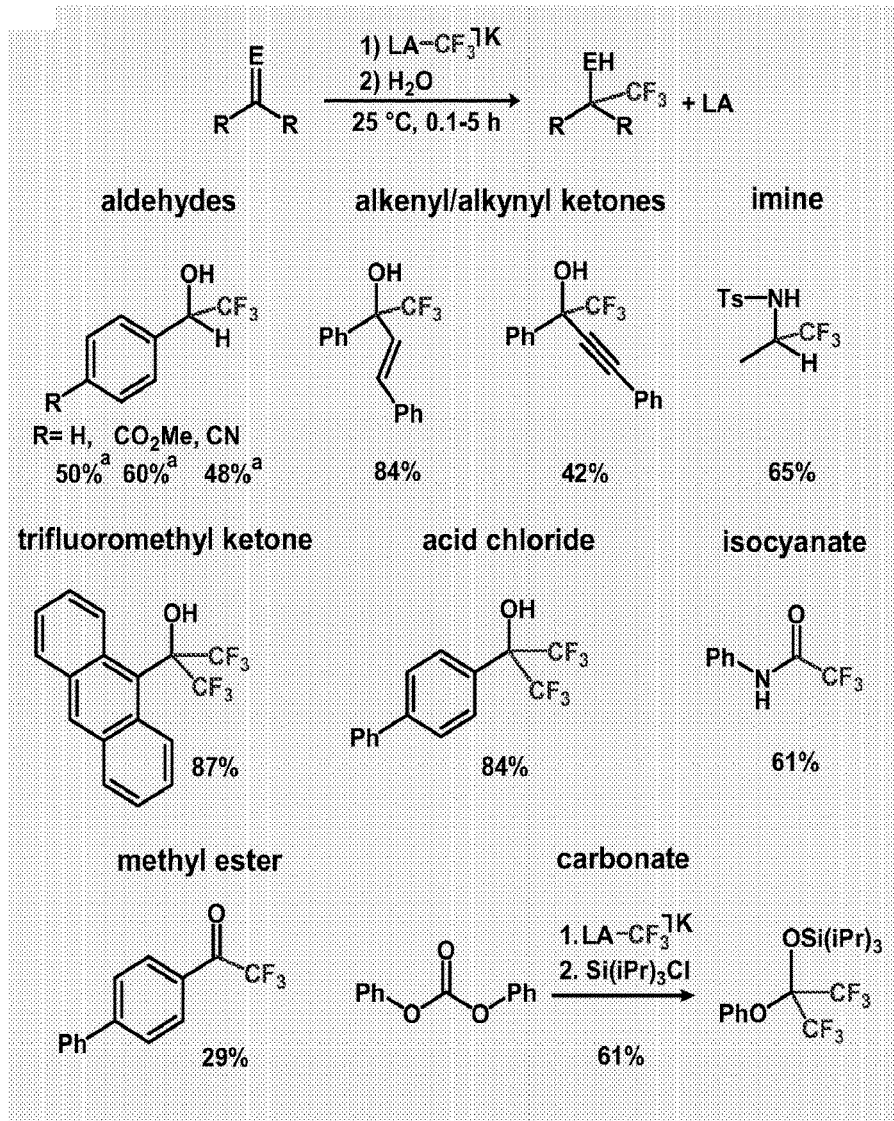
FIG. 3 shows various specific organic trifluoromethylation reactions using complexes 1 and 3.
Figure 3:
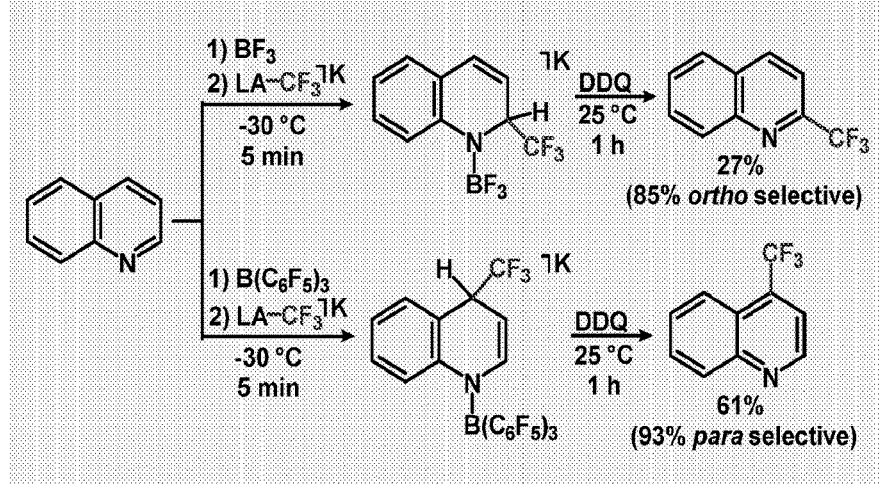
Figure 3:
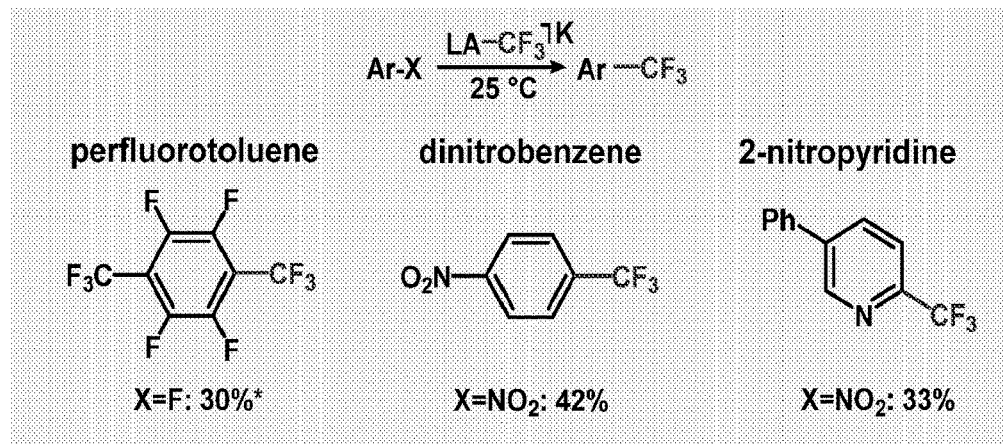
Figure 3:
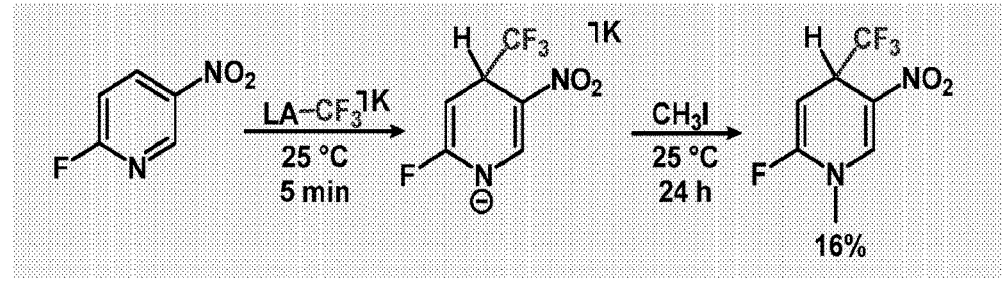
Figure 3:
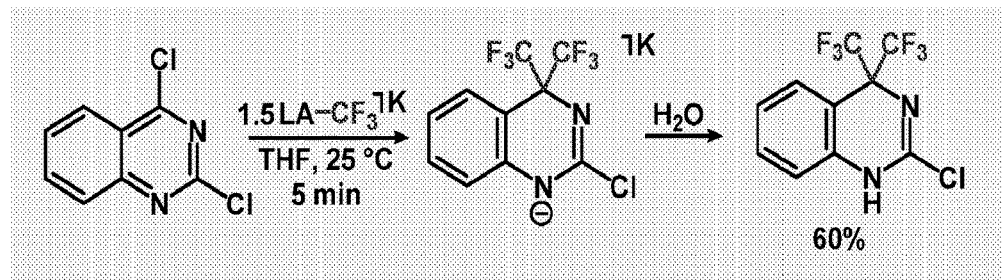
Figure 3:
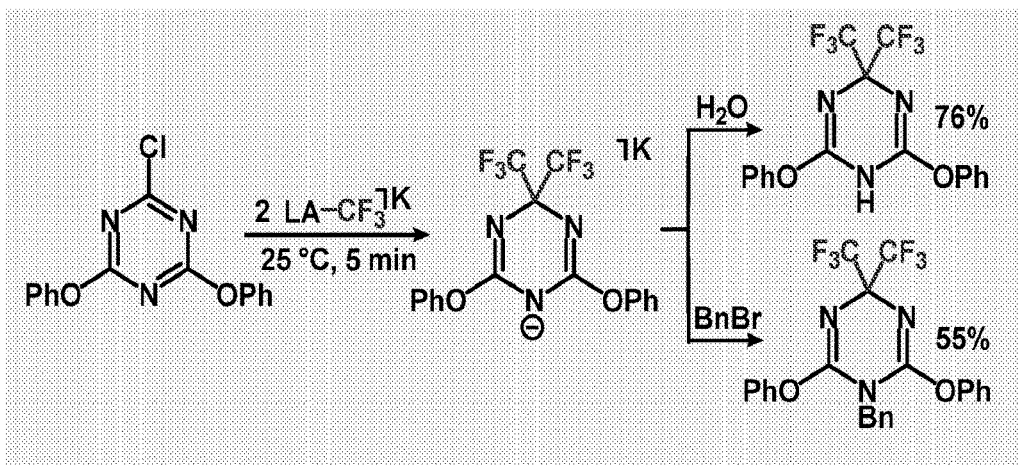
Figure 3:
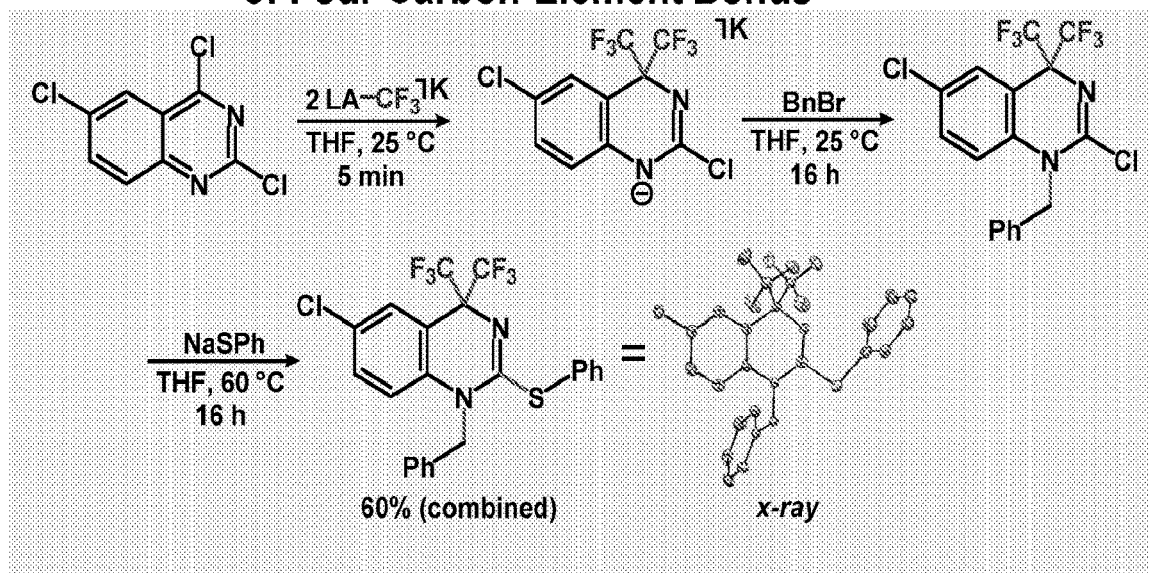

Organic Reactions:

The disclosed complexes can be used in chemical reactions on organic starting material. For example, 1 and 3 exhibit Grignard-like reactivity with organic substrates (FIG. 3). Non-enolizable aldehydes, ketones, esters, acid chlorides, imines, carbonates, isocyanates, trifluoromethyl ketones, alkynyl ketones, and vinyl ketones are all rapidly trifluoromethylated at room temperature. The lower p$K_{CF_3}$ value of $B_3N_3Me_6$ as compared to $B(OMe)_3$ translates to significantly higher reactivity of 1 as compared to 2: benzophenone is trifluoromethylated in quantitative yield in 30 minutes at room temperature while 2 provides only 2% yield under identical conditions. 1, and 3 are stable, one-component solutions without competing nucleophilic sites and should provide an economic and operational advantage to $KB(OMe)_3CF_3$ (2), $SiMe_3CF_3/CsF$ or $K(DMF.CF_3)$, which are weak nucleophiles, generate stoichiometric waste, or require low temperatures, respectively.

The high $CF_3^-$ nucleophilicity of 1 suggests that it may transfer $CF_3^-$ to electron-deficient aromatic compounds. Nucleophilic aromatic functionalization can be broadly divided between two classes, nucleophilic aromatic substitution (SNAr) and organometallic cross-coupling. These orthogonalo methods, which rely on different leaving groups, are widely used in complex molecule synthesis. However, with the exception of extremely electrophilic perfluorinated arenes nucleophilic aromatic trifluoromethylation reactions have only been demonstrated through organometallic cross-coupling; efficient SNAr trifluoromethylation reactivity is unknown because prior LA-CF3 reagents lack sufficient stability and nucleophilicity. The potent nucleophilicity of 1 enables the first high yielding SNAr reactions with sp2 centers in benzenes, pyridines, pyrimidines, and triazines. Notably, 1,4-dinitrobenzene and 2-nitro-5-phenylpyridine undergo SNAr reactions with 1, effectively transforming an aromatic nitro group into a trifluoromethyl group in an unprecedented functional group interconversion, while perfluorotoluene reacts with 1 to provide perfluoroxylene.

Although pyridine derivatives that contain good leaving groups in the 2- or 4-position can undergo classical SNAr reactions, unsubstituted pyridines do not normally react with $CF_3^-$. However, electrophilic functionalization of the nitrogen atom with Lewis acids can dramatically increase the susceptibility to nucleophilic addition of CF3-; subsequent oxidation can rearomatize the substrate in a net C—H trifluoromethylation. This was recently demonstrated using two approaches to N-functionalization: activation by the strong Lewis acid $B(C_6F_4CF_3)_3$ followed by $SiMe_3CF_3/F^-$ (for 4-selective $CF_3^-$ addition) or addition of $BF_2CF_3$ to a pyridine N-oxide (for 2-selective $CF_3^-$ addition). These activation protocols necessarily require expensive stoichiometric reagents, nucleophilic $SiMe_3CF_3$ activators that may quench Lewis acids, and/or aggressive oxidants needed to generate a pyridine N-oxide. The use of a single-component, stable, and highly nucleophilic $CF_3^-$ reagent should enable selective dearomatizing trifluoromethylations using commercially available Lewis acids and without using pyridine N-oxide substrates. Addition of 1 to quinoline substrates activated by BF3 or B(C6F5)3, followed by oxidation with DDQ, leads to either 2- or 4-C—H trifluoromethylated products with high selectivity (95-83%) and good yields. With highly electron-deficient pyridines such as 5-nitro-2-fluoropyridine, a reaction with 1 occurs without the use of any exogenous Lewis acid to provide trifluoromethylated products, and treatment with methyl iodide affords isolation of the dearomatized 4-trifluoromethylated dihydroamide (2-step isolated yield: 20%). Overall, this simple and low cost approach to heterocycle C—H trifluoromethylation uses only $HCF_3$, base, and cheap, commercially available Lewis acids as consumed reagents.

A unique aspect of the $CF_3^-$ nucleophile in SNAr reactions is that upon trifluoromethylation of an aryl halide, the substrate becomes more rather than less activated to subsequent nucleophilic addition. Thus, it is hypothesized that it may be possible to transform electron-deficient aromatic halides into dearomatized geminal bis(trifluoromethylated) products, a structurally unique motif in organic chemistry. Triazines and quinazolines react with 1 to provide the geminal bis(trifluoromethylated) products, which can then react with electrophiles and nucleophiles in selective, one-pot cascade reactions to make highly decorated products. To demonstrate the utility of this novel transformation, trichloroquinazoline was combined with 2 equiv. 1, then 1 equiv. benzyl bromide, and finally 1 equiv. sodium thiophenolate in one pot to construct four new bonds in 60% isolated yield over all steps. The highly selective reaction bis(trifluoromethylates) only the 4-position of the quinazoline, leaving the 2- and 6-chlorinated positions intact; quenching with benzyl bromide selectively alkylates the 1-amide, and addition of a second nucleophile provides a thioether in the 2-position, leaving the 6-chlorine available for further modification via catalytic cross-coupling; alternatively, the use of water in place of benzyl bromide allows isolation of the free secondary amine. Monochlorinated triazine reacts analogously, providing the bis(trifluoromethylated) tertiary and secondary amines in high yield. The new reactions, in which $HCF_3$ is directly transferred to an aromatic substrate, do not occur using previously reported direct $HCF_3$ activation systems such as KOtBu/$HCF_3$ in THF or DMF, further highlighting the unique nucleophilic reactivity enabled by 1.

Figure 4:
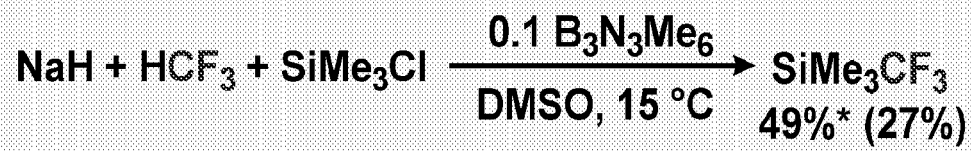
FIG. 4 shows the synthesis of CF$_3^-$, CF$_3$·, and CF$_3^+$ reagents from HCF$_3$.
Figure 4:
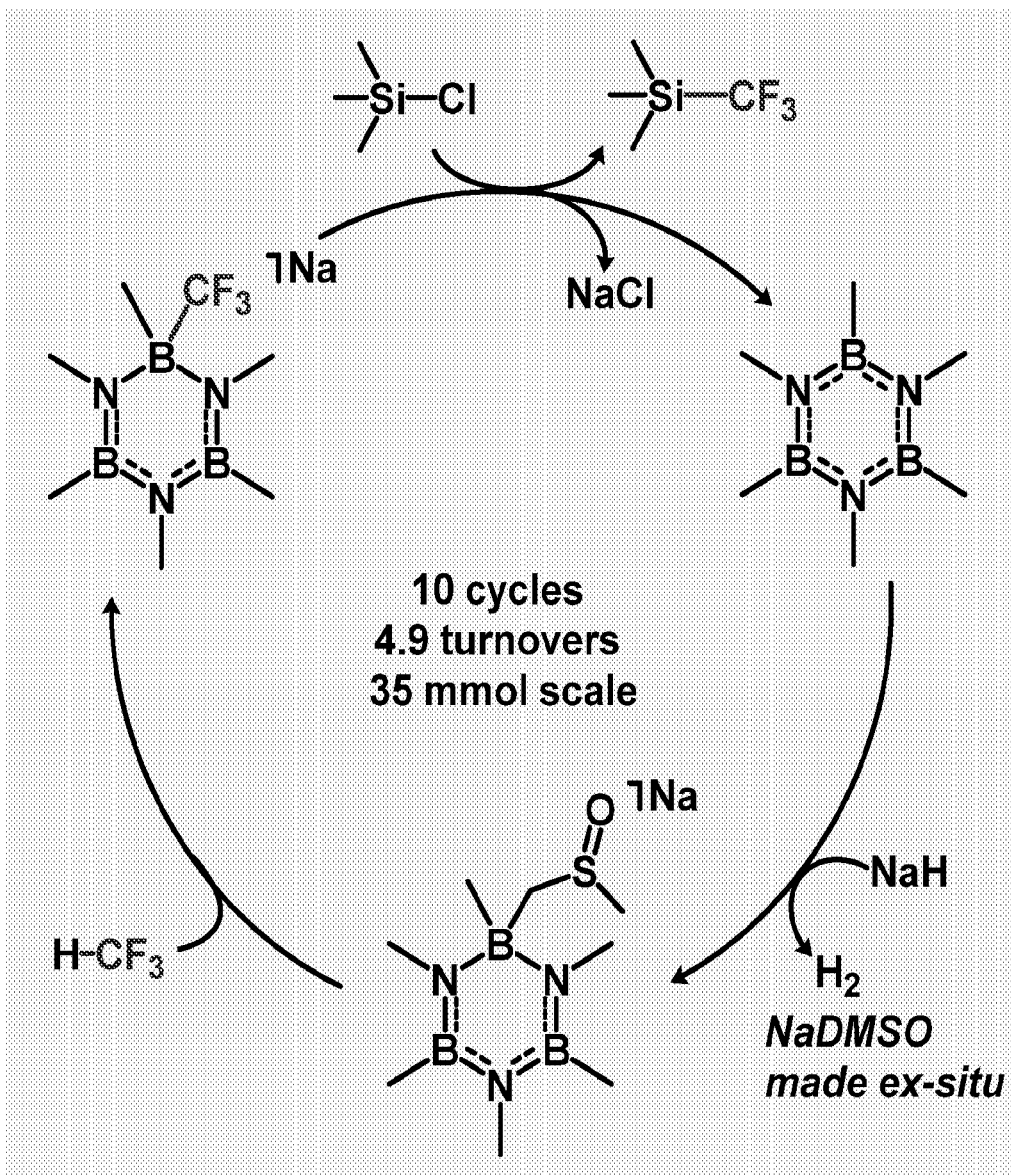
Figure 5:
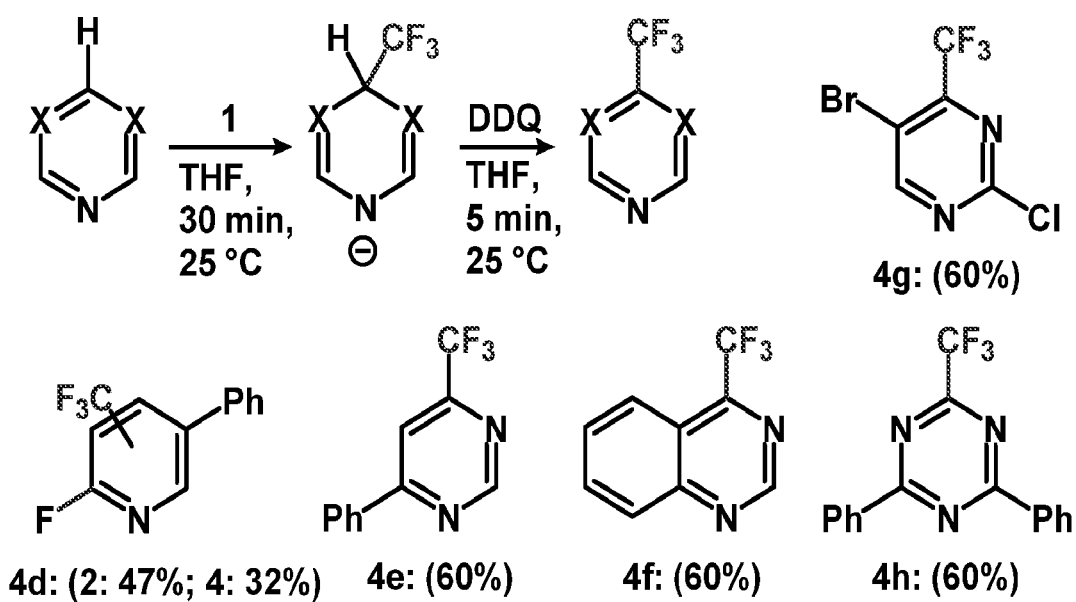
FIG. 5 shows direct nucleophilic addition/oxidation of heteroaromatic compounds.

The high cost of trifluoromethylation reagents stems from their multi-step syntheses from the ozone-depleting gas $CF_3I$. The regeneration of the thermally stable $B_3N_3Me_6$ Lewis acid in all of the reactions noted above strongly suggested that these popular reagents could be efficiently synthesized using $B_3N_3Me_6$ as a recyclable component, thereby reducing the reaction inputs to cheap base, $HCF_3$, and the direct precursor (FIG. 4). Reagents used to install the $CF_3$ group can be divided between their use for nucleophilic $CF_3^-$, radical $CF_3$., and electrophilic $CF_3^+$ transfer. The most important of these is nucleophilic $SiMe_3CF_3$, the currently used precursor to almost all other trifluoromethylation reagents. The preparation of this compound demonstrates the practical in-situ recyclability of the Lewis acid on a large scale. Through ten cycles of an iterative addition/distillation protocol, about 5 turnovers with respect to $B_3N_3Me_6$ was achieved to obtain 34 mmol $SiMe_3CF_3$ after distillation without the need for separation or purification of the borazine Lewis acid. The only consumed reagents used were NaH, $SiMe_3Cl$, and $HCF_3$, likely making this the cheapest approach to the synthesis of $SiMe_3CF_3$. The radical $CF_3$. reagent $KSO_2CF_3$ can also be easily prepared in 66% isolated yield by treating $SO_2$ with 1 (98% recovery of $B_3N_3Me_6$).

The hypervalent iodonium-CF3 reagent Togni I, an important $CF_3^+$ reagent, can be synthesized in 78% chemical yield and with 98% regeneration of B3N3Me6 by treating the iodonium chloride precursor with 1. To demonstrate the potential of this methodology for rapid synthesis of complex biomolecules, an in-situ preparation of Togni I was used for the electrophilic trifluoromethylation of a thiol-functionalized sugar. Conversion to the trifluoromethylated sugar from $HCF_3$ is complete in 32 minutes, and isolation of the solid product by flash chromatography requires a further 90 minutes (43% isolated). Since $HCF_2{}^{18}F$ can be easily prepared from $K^{18}F$ and $HCF_2I$, this methodology may be useful for the installation of radiolabeled trifluoromethyl groups for medical PET imaging applications. Direct access to these well-established nucleophilic $CF_3^-$, radical $CF_3$., and electrophilic $CF_3^+$ reagents from $HCF_3$ should help reduce the cost and increase access to the $CF_3$ group in existing large-scale processes.

The disclosure will be more fully understood by reference to the following examples which detail exemplary embodiments of the disclosure. They should not, however, be construed as limiting the scope of the disclosure. All citations throughout the disclosure are hereby expressly incorporated by reference.

EXAMPLES

General Considerations:

Hexamethylborazine, (B,B',B")trisdimethylamino-(N,N',N")trimethylborazine, (B,B',B")trismethoxy-(N,N',N")trimethylborazine, N,N,N-trimethylborazine, trisethyleneoxyborazine, tris(1,3)propyleneoxyborazine, tris-n-methylethyleneiminoborazine, tris-N-methyl(1,3)propyleneiminoborazine, 1-Chloro-1,3-dihydro-3,3-dimethyl-1,2-benziodoxole, 6-chloro-9-tosyl-9H-purine, 6-chloro-2-fluoro-9-tosyl-9H-purine, 3-nitro-1-tosyl-1H-pyrazole, 2-fluoroquinoline, benzylpotassium, dimsyl potassium, dimsyl sodium, and N-tosylbenzaldimine were prepared according to literature procedures. DMSO, pentane, THF, diethyl ether, glyme, acetonitrile, toluene, and DMF were purified using a Glass Contour solvent purification system through percolation through a Cu catalyst, molecular sieves, and alumina and finally stored over activated molecular sieves for a minimum of 48 hours. Methyl-THF was distilled from molten sodium under nitrogen. All other reagents were used from commercial sources without further purification.

NMR spectra were recorded on a Varian Vnmrs 700, Varian Inova 500, or Varian MR400 spectrometer. $^1H$, $^{13}C$, $^{19}F$, $^{11}B$, and $^{31}P$ shifts are reported in parts per million (ppm) relative to TMS, with the residual solvent peak used as an internal reference. $^{31}P$, $^{11}B$, and $^{19}F$ NMR spectra are referenced on a unified scale, where the single primary reference is the frequency of the residual solvent peak in the $^1H$ NMR spectrum. $^1H$, $^{13}C$, and $^{31}P$ multiplicities are reported as follows: singlet (s), doublet (d), triplet (t), quartet (q), and multiplet (m). Mass spectra were obtained on an electrospray TOF mass spectrometer. Crystals were mounted on a Rigaku AFC10K Saturn 944+CCD-based X-ray diffractometer equipped with a low temperature device and Micromax-007HF Cu-target micro-focus rotating anode ($\lambda$=1.54187 Å) operated at 1.2 kW power (40 kV, 30 mA). The X-ray intensities were measured at 85(1) K with the detector placed at a distance 42.00 mm from the crystal; the data were processed with CrystalClear 2.011 and corrected for absorption. The structures were solved and refined with the Olex2[3] software package and ShelXL.[4]

Syntheses

Preparation of M(LA-CF3) Stock Solutions from $HCF_3$ $K(B(OMe)_3CF_3$: $B(OMe)_3$ (5.0 mmol, 0.56 mL) was dissolved in 21.8 mL DMSO in a 100 mL single-neck round bottom flask equipped with a large teflon-coated magnetic stirbar, which was then sealed with a tightly belt-clamped septum. Dimsyl potassium (1.93 M, 5.0 mmol, 2.59 mL) was then rapidly added via syringe, and the mixture vigorously stirred for 15 seconds. Gaseous $HCF_3$ was then immediately added to the sealed vessel with a 60 mL syringe (6.0 mmol, 148 mL) and continuous efficient stirring. The light yellow homogeneous solution was stirred for 10 minutes. $^{19}F$ NMR showed 96% yield of $K(B(OMe)_3CF_3$. $t_{1/2}$ ($^{19}F$ NMR, 25° C.): >5 months $K(BOCH_2CH_2N)_3CF_3$: Trisethyleneoxyborazine (10.5 mmol, 2.169 g) was suspended in 43 mL DMSO in a 100 mL single-neck round bottom flask equipped with a large teflon-coated magnetic stirbar, which was then sealed with a tightly belt-clamped septum. Dimsyl potassium (1.93 M, 10 mmol, 5.18 mL) was then rapidly added via syringe, and the mixture vigorously stirred for 30 minutes. After this time, the reaction became homogeneous. Gaseous $HCF_3$ was added to the sealed vessel with a 60 mL syringe (12 mmol, 297 mL) and continuous efficient stirring. The light yellow homogeneous solution was stirred for 10 minutes. 19F NMR showed 99% yield of $K(BOCH_2CH_2N)_3CF_3$ (based on KDMSO). $t_{1/2}$ ($^{19}F$ NMR, 25° C.): >5 months $K(B_3N_3Me_6)CF_3$: Hexamethylborazine (2.7 mmol, 0.443 g) was suspended in 13 mL DMSO in a 20 mL single-neck conical flask equipped with a large teflon-coated magnetic stirbar, which was then sealed with a tightly belt-clamped septum. Dimsyl potassium (1.80 M, 2.7 mmol, 1.5 mL) was then rapidly added via syringe, and the mixture vigorously stirred for 30 minutes. After this time, the reaction became homogeneous. Gaseous HCF$_3$ was added to the sealed vessel with a 60 mL syringe (12 mmol, 297 mL) and continuous efficient stirring. The light yellow homogeneous solution was stirred for 10 minutes. $^{19}$F NMR showed >99% yield of K(BOCH$_2$CH$_2$N)$_3$CF$_3$. $t_{1/2}$ ($^{19}$F NMR, 25° C.): 17 days K(18-crown-6)(B$_3$N$_3$Me$_6$)CF$_3$(THF): Hexamethylborazine (2.7 mmol, 0.443 g) and 18-crown-6 (2.7 mmol, 0.712 g) were dissolved in 11 mL THF in a 20 mL single-neck conical flask equipped with a large teflon-coated magnetic stirbar. The vessel was then allowed to cool to 0° C. in a glovebox cold-well for one hour with gentle stirring. Benzylpotassium (2.7 mmol, 0.350 g) was then quickly added to this cold solution, and the initial deep red color of dissolved benzylpotassium quickly changed to a faint purple color. The homogeneous solution was stirred for 10 minutes, giving a homogeneous purple solution. The flask was then sealed with a tightly belt-clamped septum. Gaseous HCF$_3$ was added to the sealed vessel with a 60 mL syringe (3.3 mmol, 75 mL) and continuous efficient stirring. The faint pink homogeneous solution was stirred for 10 minutes. $^{19}$F NMR showed >99% yield of K(B$_3$N$_3$Me$_6$CF$_3$).

Nucleophilic Trifluoromethylation of Organic Compounds with HCF$_3$-Derived M(LA-CF$_3$): Condition Screening To 0.1 mmol of substrate dissolved in 0.5 mL DMSO or THF was added a stock solution of HCF$_3$ derived CF$_3^-$ reagent as noted below for each of Methods A-D. NMR spectra were recorded at 30 minute, 1 hour, 5 hour, and 24 hour time points to monitor conversion to trifluoromethylated products.

Method A:

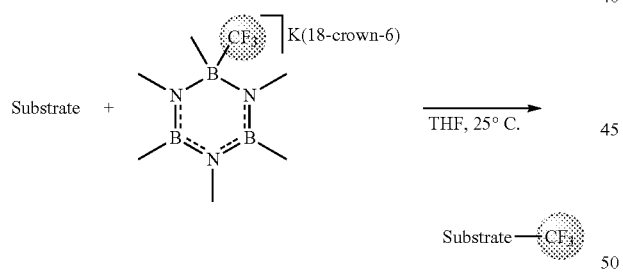

Method B:

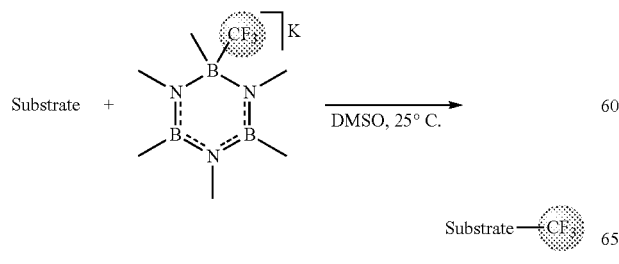

Method C:

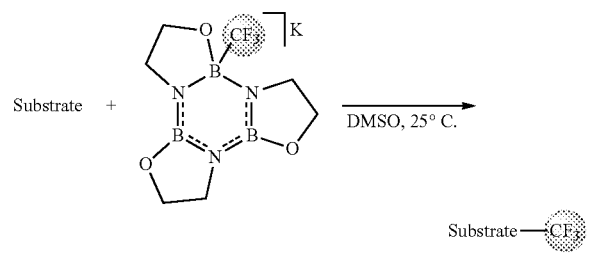

Method D:

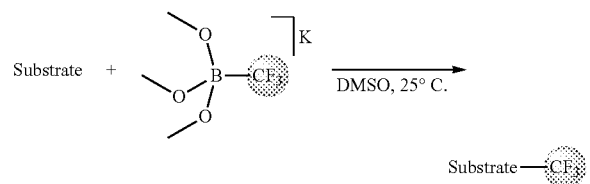

(E)-chalcone

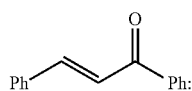

Method A: 30 min: 19%; 5 h: 21%; 72 h: 20%
Method B: 30 min: 58%; 5 h: 37%; 24 h: 6%; 72 h: 0%
Method C: 30 min: 19%; 5 h: 17%; 24 h: 5%; 72 h: 0%
Method D: 30 min: 3.5%; 5 h: 3.3%; 24 h: 1.7%; 72 h: 0%
1,3-Diphenylprop-2-yn-1-one

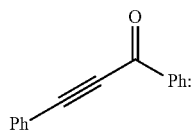

Method A: 30 min: 75%; 5 h: 76%; 72 h: 77%
Method B: 30 min: 4.6%; 5 h: 2.0%; 72 h: 0.4%
Method C: 30 min: 9%; 5 h: 8%; 24 h: 7%; 72 h: 5%
Method D: 30 min: 10%; 5 h: 12%; 24 h: 12%; 72 h: 12%
Benzophenone

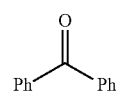

Method A: 30 min: 75%; 5 h: 76%; 72 h: 77%
Method B: 30 min: 4756%; 5 h: 2.0%; 72 h: 0774%
Method C: 30 min: 9%; 5 h: 8%; 24 h: 7%; 72 h: 5%
Method D: 30 min: 10%; 5 h: 12%; 24 h: 12%; 72 h: 12%
Benzoyl chloride

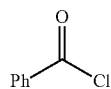

Method A: 30 min: 90%; 5 h: 95%; 24 h: 93% 72 h: 93%
2 EQ KCF$_3$: 30 min: 74%; 5 h: 100%; 24 h: 100% 72 h: 100%
2,2,2-trifluoro-1-phenylethan-1-one

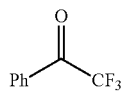

Method A: 30 min: 100%; 5 h: 100%; 24 h: 100% 72 h: 100%
Method B: 30 min: 92%; 5 h: 100%; 24 h: 87% 72 h: 90%
Method C: 30 min: 100%; 5 h: 100%; 24 h: 100%; 72 h: 100%
Method D: a) 30 min: 38%; 5 h: 1%; 24 h: 0%; 72 h: 0%
b) 30 min: 76%; 5 h: 119%; 24 h: 133%; 72 h: 130%
Benzaldehyde

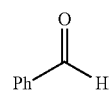

Method A: 30 min: 85%; 5 h: 11%; 24 h: 0% 72 h: 0%
Method B: 30 min: 80%; 5 h: 71%; 24 h: 77% 72 h: 75%
Method C: 30 min: 95%; 5 h: 100%; 24 h: 100%; 72 h: 98%
Method D: 30 min: 26%; 5 h: 76%; 24 h: 77%; 72 h: 81%
Methyl 4-formylbenzoate

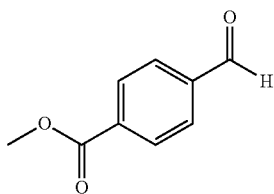

Method A: 30 min: 25%; 5 h: 29%; 24 h: 26% 72 h: 25%
Method B: 30 min: 57%; 5 h: 0%; 24 h: 0% 72 h: 0%
Method C: 30 min: 93%; 5 h: 92%; 24 h: 92%; 72 h: 79%
Method D: 30 min: 25%; 5 h: 72%; 24 h: 73%; 72 h: 73%
4-(dimethylamino)benzaldehyde

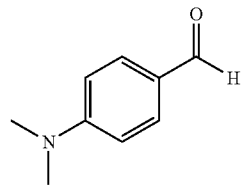

Method A: 30 min: 88%; 5 h: 86%; 24 h: 80% 72 h: 78%
Method B: 30 min: 57%; 5 h: 32%; 24 h: 52% 72 h: 53%
Method C: 30 min: 56%; 5 h: 59%; 24 h: 51%; 72 h: 42%
Method D: 30 min: 14%; 5 h: 56%; 24 h: 58%; 72 h: 59%
4-formylbenzonitrile

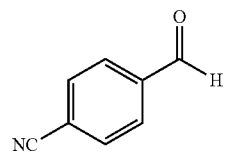

Method A: 30 min: 32%; 5 h: 28%; 24 h: 23% 72 h: 20%
Method B: 30 min: 38%; 5 h: 0%; 24 h: 0% 72 h: 0%
Method C: 30 min: 88%; 5 h: 88%; 24 h: 84%; 72 h: 62%
Method D: 30 min: 22%; 5 h: 51%; 24 h: 50%; 72 h: 49%
Methyl benzoate

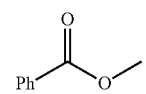

Method A: a) 30 min: 5%; 5 h: 30%; 72 h: 83%
b) 30 min: 64%; 5 h: 52%; 72 h: 20%
Method B: 30 min: 0%; 5 h: 0%; 24 h: 0% 72 h: 0%
Method C: 30 min: 0%; 5 h: 0%; 24 h: 0% 72 h: 0%
Method D: 30 min: 0%; 5 h: 0%; 24 h: 0% 72 h: 0%
Benzoic anhydride

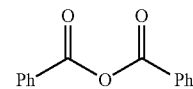

Method A: 30 min: 54%; 5 h: 58%; 24 h: 58% 72 h: 53%
Method B: 30 min: 20%; 5 h: 25%; 24 h: 27% 72 h: 27%
Method C: 30 min: 39%; 5 h: 35%; 24 h: 41%; 72 h: 41%
Method D: 30 min: 65%; 5 h: 37%; 24 h: 1%; 72 h: 0%
Diphenyl carbonate

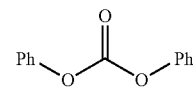 [SMILES: O=C(Oc1ccccc1)Oc1ccccc1]

Method A: 30 min: 98%; 5 h: 100%; 24 h: 100% 72 h: 100%
Method B: 30 min: 65%; 5 h: 62%; 24 h: 46% 72 h: 32%
Method C: 30 min: 50%; 5 h: 58%; 24 h: 61%; 72 h: 53%
Method D: 30 min: 0%; 5 h: 36%; 24 h: 54%; 72 h: 62%
Isocyanatobenzene

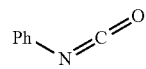

Method A: 30 min: 92%; 5 h: 96%; 24 h: 98% 72 h: 96%
Method B: 30 min: 16%; 5 h: 18%; 24 h: 18% 72 h: 18%
Method C: 30 min: 6%; 5 h: 8%; 24 h: 8% 72 h: 8%
Method D: 30 min: 0.7%; 5 h: 2.1%; 24 h: 5.0%; 72 h: 7.5%
(E)-N-benzylidene-4-methylbenzenesulfonamide

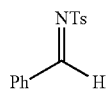

Method A: 30 min: 99%; 5 h: 99%; 72 h: 99%
Method B: 30 min: 95%; 5 h: 91%; 24 h: 96% 72 h: 93%
Method C: 30 min: 98%; 5 h: 100%; 24 h: 100%; 72 h: 98%
Method D: 30 min: 22%; 5 h: 63%; 24 h: 85%; 72 h: 90%
4-fluorobenzonitrile

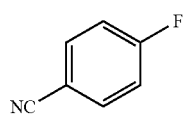

Method A: 30 min: 0.5%; 5 h: 1.9%; 24 h: 3.2% 72 h: 3.9%
Method B: 30 min: 0%; 5 h: 0%; 24 h: 0% 72 h: 0%
Method C: 30 min: 0%; 5 h: 0%; 24 h: 0% 72 h: 0%
Method D: 30 min: 0%; 5 h: 0%; 24 h: 0% 72 h: 0%
2-nitropyridine

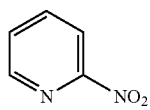

Method A: a) 30 min: 21%; 5 h: 30%; 72 h: 32%
b) 30 min: 21%; 5 h: 21%; 72 h: 31%
Method B: 30 min: 0.1%; 5 h: 0%; 24 h: 0% 72 h: 0%
Method C: 30 min: 0%; 5 h: 0%; 24 h: 0% 72 h: 0%
Method D: 30 min: 0%; 5 h: 0%; 24 h: 0% 72 h: 0%
1,2,3,4,5-pentafluoro-6-(trifluoromethyl)benzene

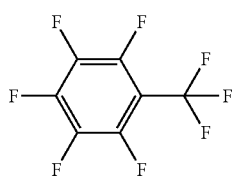 [SMILES: Fc1c(F)c(F)c(C(F)(F)F)c(F)c1F]

Method A: 30 min: 30%; 5 h: 30%; 72 h: 30%
Method B: 30 min: 25%; 5 h: 20%; 24 h: 20% 72 h: 19%
Method C: 30 min: 15%; 5 h: 22%; 24 h: 17% 72 h: 10%
Method D: 30 min: 14%; 5 h: 21%; 24 h: 19% 72 h: 20%
1,4-dinitrobenzene

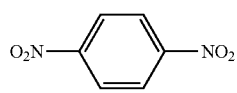 [SMILES: O=[N+]([O-])c1ccc([N+](=O)[O-])cc1]

Method A: 30 min: 41%; 5 h: 48%; 24 h: 54% 72 h: 58%
Method B: 30 min: 0.1%; 5 h: 0.7%; 24 h: 1.5% 72 h: 1.5%
Method C: 30 min: 15%; 5 h: 19%; 24 h: 24% 72 h: 27%
Method D: 30 min: 0.7%; 5 h: 2%; 24 h: 6% 72 h: 9%
1-fluoro-2-nitrobenzene

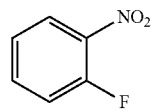

Method A: 30 min: 0.5%; 5 h: 1.9%; 24 h: 3.2% 72 h: 3.9%
Method B: 30 min: 0%; 5 h: 0%; 24 h: 0% 72 h: 0%
Method C: 30 min: 0%; 5 h: 0%; 24 h: 0% 72 h: 0%
Method D: 30 min: 0%; 5 h: 0%; 24 h: 0% 72 h: 0%
4-nitrobenzonitrile

Method A: 30 min: 7.2%; 5 h: 7.2%; 24 h: 7.2% 72 h: 5.6%
Method B: 30 min: 0%; 5 h: 0%; 24 h: 0% 72 h: 0%
Method C: 30 min: 0%; 5 h: 0%; 24 h: 0% 72 h: 0%
Method D: 30 min: 0%; 5 h: 0%; 24 h: 0% 72 h: 0%
2-nitro-1-tosyl-1H-pyrazole

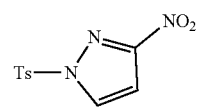

Method A: 30 min: 1.4%; 5 h: 1.4%; 24 h: 1.4% 72 h: 1.4%
Method B: 30 min: 0%; 5 h: 0%; 24 h: 0% 72 h: 0%
Method C: 30 min: 3.7%; 5 h: 4.9%; 24 h: 5.4% 72 h: 5.0%
Method D: 30 min: 0%; 5 h: 0.5%; 24 h: 1% 72 h: 1%
5-bromo-2-nitropyridine

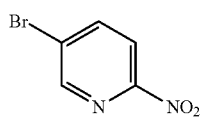

Method A: 30 min: 8.6%; 5 h: 8.6%; 24 h: 8.6% 72 h: 7.6%
Method B: 30 min: 0%; 5 h: 0.1%; 24 h: 0.1% 72 h: 0.2%
Method C: 30 min: 3.6%; 5 h: 5.9%; 24 h: 6.4% 72 h: 6.4%
Method D: 30 min: 0.3%; 5 h: 0.8%; 24 h: 1.8% 72 h: 2.8%
3-chloro-2-nitropyridine

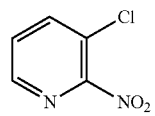

Method A: 30 min: 3.7%; 5 h: 3.7%; 24 h: 3.7% 72 h: 3.7%
Method B: 30 min: 0%; 5 h: 0.5%; 24 h: 0.6% 72 h: 0.6%
Method C: 30 min: 3.0%; 5 h: 5.1%; 24 h: 5.2% 72 h: 5.4%
Method D: 30 min: 0.3%; 5 h: 0%; 24 h: 0% 72 h: 0%
3-ethoxy-2-nitropyridine

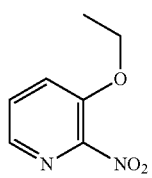

Method A: 30 min: 3%; 5 h: 4%; 24 h: 7% 72 h: 10%
Method B: 30 min: 0%; 5 h: 0%; 24 h: 0% 72 h: 0%
Method C: 30 min: 0%; 5 h: 0%; 24 h: 0% 72 h: 0%
Method D: 30 min: 0%; 5 h: 0%; 24 h: 0% 72 h: 0%
5-chloro-3-methyl-1-phenyl-1H-pyrazole

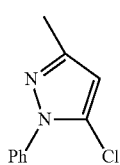

Method A: 30 min: 0%; 5 h: 0%; 24 h: 0% 72 h: 0%
Method B: 30 min: 0%; 5 h: 0%; 24 h: 0% 72 h: 0%
Method C: 30 min: 0%; 5 h: 0%; 24 h: 0% 72 h: 0%
Method D: 30 min: 0%; 5 h: 0%; 24 h: 0% 72 h: 0%
Pyridine 1-oxide

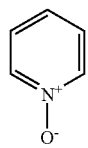

Method A: 30 min: 3%; 5 h: 9%; 72 h: 20%
Method B: 30 min: 0%; 5 h: 0.2%; 24 h: 0% 72 h: 0%
Method C: 30 min: 0%; 5 h: 0%; 24 h: 0% 72 h: 0%
Method D: 30 min: 0%; 5 h: 0%; 24 h: 0% 72 h: 0%
2-chloro-5-(trifluoromethyl)pyridine

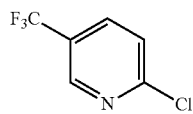

Method A: 30 min: 23%; 5 h: 0%; 72 h: 0%
Method B: 30 min: 10%; 5 h: 10%; 24 h: 10%
Method C: 30 min: 15%; 5 h: 15%; 24 h: 16% 72 h: 14%
Method D: 30 min: 14%; 5 h: 15%; 24 h: 13% 72 h: 14%
2-chloro-5-nitropyridine

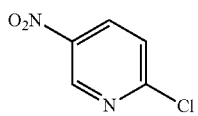

Method A: a) 30 min: 24%; 5 h: 29%; 72 h: 3%
b) 30 min: 1$^8$%; 5 h: 22%; 72 h: 15%
Method B: a) 30 min: 22%; 5 h: 24%; 24 h: 24% 72 h: 23%
b) 30 min: 12%; 5 h: 13%; 24 h: 13% 72 h: 13%
Method C: a) 30 min: 41%; 5 h: 44%; 24 h: 45% 72 h: 45%
b) 30 min: 34%; 5 h: 36%; 24 h: 37% 72 h: 37%
Method D: a) 30 min: 5%; 5 h: 12%; 24 h: 1$^8$% 72 h: 19%
b) 30 min: 6%; 5 h: 15%; 24 h: 22% 72 h: 24%
2-fluoro-5-nitropyridine

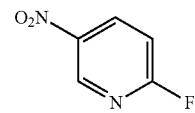

Method A: a) 30 min: 50%; 5 h: 51%; 72 h: 47%
b) 30 min: 36%; 5 h: 24%; 72 h: 10%
Method B: a) 30 min: 61%; 5 h: 58%; 24 h: 58% 72 h: 56%
b) 30 min: 21%; 5 h: 17%; 24 h: 12% 72 h: 12%
Method C: a) 30 min: 47%; 5 h: 50%; 24 h: 50% 72 h: 50%
b) 30 min: 17%; 5 h: 17%; 24 h: 17% 72 h: 17%
Method D: a) 30 min: 6%; 5 h: 6%; 24 h: 5% 72 h: 4%
b) 30 min: 11%; 5 h: 20%; 24 h: 24% 72 h: 25%
2-fluoroquinoline

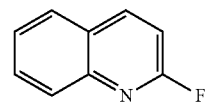 [SMILES: Fc1ccc2ccccc2n1]

Method A: 30 min: 2.3%; 5 h: 8.4%; 72 h: 13%
Method B: 30 min: 0%; 5 h: 0%; 24 h: 0% 72 h: 0%
Method C: 30 min: 0%; 5 h: 1%; 24 h: 2% 72 h: 3%
Method D: 30 min: 0%; 5 h: 0.6%; 24 h: 1.2% 72 h: 1.4%
6-chloro-N$^2$-ethyl-N$^4$-isopropyl-1,3,5-triazine-2,4-diamine

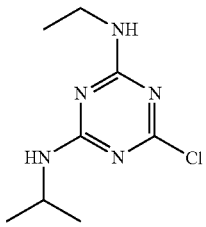

Method A: 30 min: 0%; 5 h: 0%; 24 h: 0% 72 h: 0%
Method B: 30 min: 0%; 5 h: 0%; 24 h: 0% 72 h: 0%
Method C: 30 min: 0%; 5 h: 0%; 24 h: 0% 72 h: 0%
Method D: 30 min: 0%; 5 h: 0%; 24 h: 0% 72 h: 0%
2,4-dichloro-5-methylpyrimidine

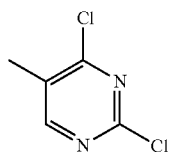

Method A: 30 min: 22%; 5 h: 0%; 24 h: 0% 72 h: 0%
Method B: 30 min: 69%; 5 h: 69%; 24 h: 31% 72 h: 0%
Method C: 30 min: 58%; 5 h: 79%; 24 h: 78% 72 h: 56%
Method D: 30 min: 5%; 5 h: 13%; 24 h: 26% 72 h: 36%
2,4-dichloroquinazoline

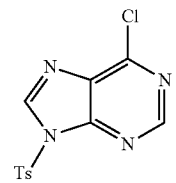

Method A: 30 min: 0%; 5 h: 0.4%; 24 h: 2.1% 72 h: 5.2%
Method B: 30 min: 0%; 5 h: 0%; 24 h: 0% 72 h: 0%
Method C: 30 min: 5%; 5 h: 4%; 24 h: 3% 72 h: 1%
Method D: 30 min: 24%; 5 h: 0%; 24 h: 0% 72 h: 0%
6-chloro-2-fluoro-9-tosyl-9H-purine

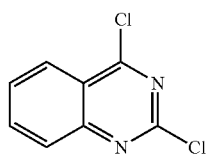 [SMILES: Clc1nc(Cl)c2ccccc2n1]

Method A: 30 min: 100%; 5 h: 98%; 24 h: 100% 72 h: 95%
Method B: 30 min: 75%; 5 h: 70%; 24 h: 70% 72 h: 66%
Method C: 30 min: 59%; 5 h: 63%; 24 h: 62% 72 h: 61%
Method D: 30 min: 16%; 5 h: 50%; 24 h: 56% 72 h: 46%
2,4,6-trichloro-1,3,5-triazine

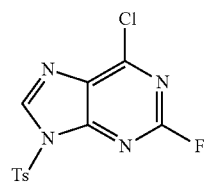

Method A: 30 min: 0%; 5 h: 0%; 24 h: 0% 72 h: 0%
Method B: 30 min: 8%; 5 h: 8%; 24 h: 8% 72 h: 8%
Method C: 30 min: 9%; 5 h: 24 h: 12% 72 h: 14%
Method D: 30 min: 5 h: 22%; 24 h: 1$^8$% 72 h: 13%
4-bromobenzenediazonium tetrafluoroborate

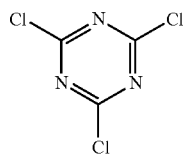

Method A: 30 min: 17%; 5 h: 19%; 24 h: 18% 72 h: 18%
2-chloro-4,6-dimethoxy-1,3,5-triazine

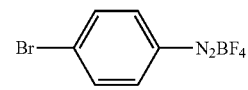

Method A: 30 min: 5%; 5 h: 5%; 72 h: 0%
Method B: 30 min: 3%; 5 h: 5%; 24 h: 0% 72 h: 0%
Method C: 30 min: 13%; 5 h: 24%; 24 h: 30% 72 h: 30%
Method D: 30 min: 61%; 5 h: 0%; 24 h: 0% 72 h: 0%
(Bromomethyl)benzene

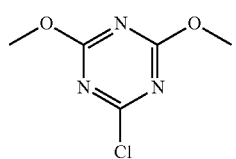

Method A: a) 30 min: 87%; 5 h: 91%; 24 h: 79%; 72 h: 41%
b) 30 min: 0%; 5 h: 0%; 24 h: 3.2%; 72 h: 41%
Method B: a) 30 min: 61%; 5 h: 39%; 24 h: 0% 72 h: 0%
b) 30 min: 0%; 5 h: 12%; 24 h: 32% 72 h: 24%
Method C: a) 30 min: 44%; 5 h: 54%; 24 h: 0% 72 h: 0%
b) 30 min: 0%; 5 h: 0%; 24 h: 52% 72 h: 51%
Method D: a) 30 min: 0%; 5 h: 2%; 24 h: 6% 72 h: 6.2%
6-chloro-9-tosyl-9H-purine

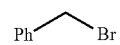

Method A: 30 min: 12%; 5 h: 12%; 72 h: 12%
Method B: 30 min: 2%; 5 h: 2%; 24 h: 2% 72 h: 2%
Method C: 30 min: 0%; 5 h: 0%; 24 h: 0% 72 h: 0%
Method D: 30 min: 0%; 5 h: 0%; 24 h: 0% 72 h: 0%

Nucleophilic Trifluoromethylation of Inorganic Compounds with M(LA-CF$_3$): Condition Screening General Protocol: To 0.1 mmol of substrate dissolved in 0.5 mL DMSO or THF was added K(B$_3$N$_3$Me$_6$)CF$_3$ of HCF$_3$ derived CF$_3^-$ reagent as a solution in matching solvent. NMR spectra were recorded at 30 minute, 1 hour, 5 hour, and 24 hour time points to monitor conversion to trifluoromethylated products. In the table below, as well as in FIG. 2, representative values for the following reactions are provided:

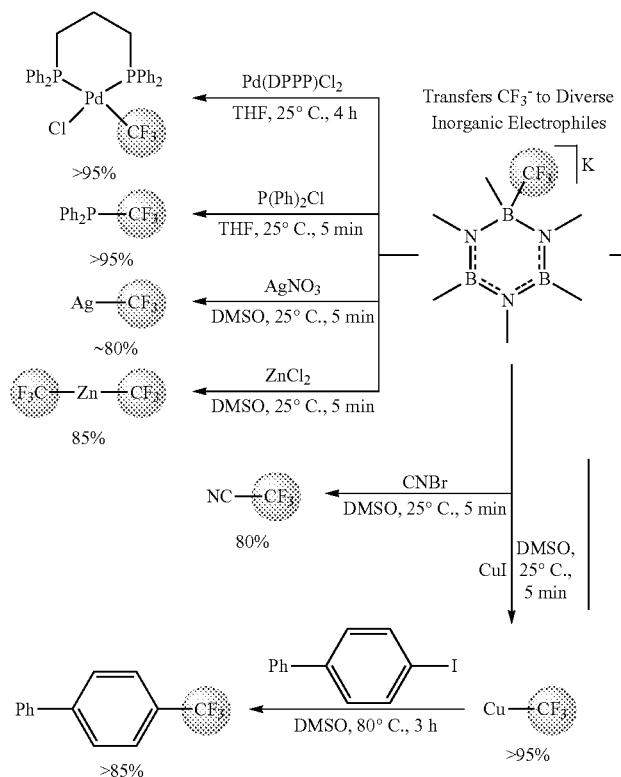
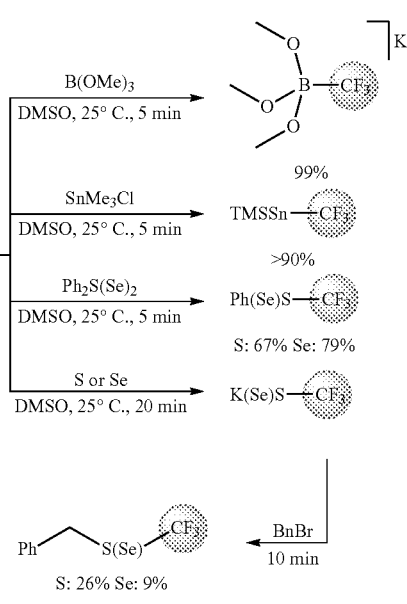

Nucleophilic Trifluoromethylation of Organic Compounds with M(LA-CF$_3$): Isolated Compounds and Characterization General Protocol: An appropriate quantity of a 0.2 M stock solution of K(LA-CF$_3$) was added to a 0.2 M solution of substrate in a 20 mL scintillation vial. The mixture was then stirred until the reaction was complete, then quenched with the addition of 15 mL of 5% aqueous HCl or saturated aqueous ammonium chloride. The product was then extracted into DCM (5×3 mL DCM) and the organic phase dried with a minimum quantity of MgSO$_4$. The dried organic phase was then filtered, concentrated to 1 mL, then purified by silica chromatography using a Biotage Isolera automated flash chromatography apparatus. The collected fractions were concentrated by rotary evaporation and under high vacuum to afford the pure products.

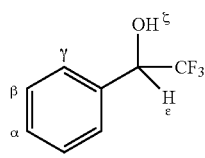

1-Phenyl-1-trifluoromethylmethanol

Substrate: Benzaldehyde. Conditions: LA: K(BOCH$_2$CH$_2$N)$_3$CF$_3$. 1.0 equivalents K(LA-CF$_3$) used. 0.40 mmol substrate. Reaction time: 1 hour. Quench: 5% HCl. Chromatography conditions: 100% DCM, 9 column volumes, 10 g SiO$_2$, flow rate 1 column volume per minute. 62 mg colorless oil, 88%. Due to the volatile nature of the product it could not be dried under high vacuum. $^1$H-NMR (CDCl$_3$): 7.46 (ß, 2H, m), 7.41 (α, γ, 3H, m), 4.98 (ε, 1H, q, $J_{1H-19F}$=6.7)), 2.88 (ζ, 1H, s). $^{13}$C-NMR: 133.92, 129.53, 128.60, 127.41, 124.22 (q, $J_{13C-19F}$=282), 72.79 (q, $J_{13C-19F}$=32). $^{19}$F-NMR: −78.36 (d, $J_{19F-1H}$=6.7). HRMS (ESI−): 221.0435 (M+HCO$_2$: 221.0431).

1,1-bistrifluoromethyl-1-phenylmethanol

Substrate: 2,2,2-trifluoromethylacetophenone. Conditions: LA: K(BOCH$_2$CH$_2$N)$_3$CF$_3$. 1.0 equivalents K(LA-CF$_3$) used. 0.40 mmol substrate. Reaction time: 5 hours. Quench: 5% HCl. Chromatography conditions: 0-100% Hexane/ethyl acetate, 8 column volumes, 10 g SiO$_2$, flow rate 1 column volume per minute. 83.6 mg colorless oil. Due to the volatile nature of the product, it was not dried under high vacuum and was therefore isolated as a mixture with ethyl acetate: 58% 1,1-bistrifluoromethyl-1-phenylethanol, 42% ethyl acetate. 50% yield. $^1$H-NMR (CDCl$_3$): 7.72 (γ, 2H, (d, $J_{1H-1H}$=7.6)), 7.48 (α, ß, 3H, m), 3.72 (ε, 1H, s). $^{13}$C-NMR: 129.99, 129.90, 128.42, 126.59, 122.75 (q, $J_{13C-19F}$=288). $^{19}$F-NMR: −75.51 (s). HRMS (ESI−): 244.0323 (M+H: 244.0250).

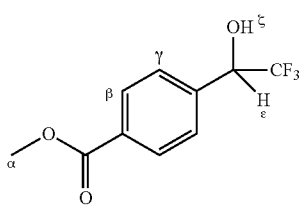 [SMILES: COC(=O)c1ccc(C(O)C(F)(F)F)cc1]

Methyl 4-(trifluoro-1-ethanol)benzoate

Substrate: Methyl 4-formyl benzoate. Conditions: LA: K(BOCH$_2$CH$_2$N)$_3$CF$_3$. 1.0 equivalents K(LA-CF$_3$) used. 0.40 mmol substrate. Reaction time: 1 hours. Quench: 5% HCl. Chromatography conditions: 0-100% Hexane/ethyl acetate, 16 column volumes, 50 g SiO$_2$, flow rate 0.5 column volume per minute. 56 mg white solid, 60%. $^1$H-NMR (CDCl$_3$): 8.00 (ß, 2H, (d, J$_{1H-1H}$=8.1)), 7.54 (γ, 2H, (d, J$_{1H-1H}$=7.9)), 5.08 (ε, 1H, (q, J$_{1H-19F}$=6.7)), 3.89 (α, 3H, s), 3.72 (ζ, 1H, s). $^{13}$C-NMR: 167.00, 139.02, 130.83, 129.69, 127.51, 124.02 (q, J$_{13C-19F}$=282), 72.25 (q, J$_{13C-19F}$=32), 52.39. $^{19}$F-NMR: −78.18 (d, J$_{19F-1H}$=6.7). HRMS (ESI-): 235.0573 (M−H: 235.0577).

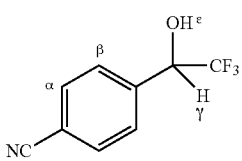 [SMILES: N#Cc1ccc(C(O)C(F)(F)F)cc1]

4-(trifluoro-1-ethanol)benzonitrile

Substrate: 4-formyl-benzonitrile. Conditions: LA: K(BOCH$_2$CH$_2$N)$_3$CF$_3$. 1.0 equivalents K(LA-CF$_3$) used. 0.40 mmol substrate. Reaction time: 1 hours. Quench: 5% HCl. Chromatography conditions: 0-100% DCM/ethyl acetate, 8 column volumes, 10 g SiO$_2$, flow rate 1 column volume per minute. 39 mg white solid, 48%. $^1$H-NMR (CDCl$_3$): 7.68 (ß, 2H, (d, J$_{1H-1H}$=8.2)), 7.63 (α, 2H, (d, J$_{1H-1H}$=8.1)), 5.11 (γ, 1H, (p, J$_{1H-19F}$=6.2)), 3.44 (ε, 1H, (d, J$_{1H-1H}$=4.6))). $^{13}$C-NMR: 139.19, 132.28, 128.27, 123.78 (q, J$_{13C-19F}$=282), 118.27, 112.94, 72.25 (q, J$_{13C-19F}$=32). $^{19}$F-NMR: −78.18 (d, J$_{19F-1H}$=6.4). HRMS (ESI-): 200.0322 (M−H: 200.0329).

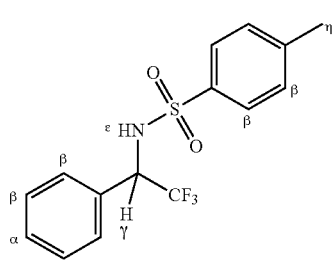 [SMILES: Cc1ccc(S(=O)(=O)NC(c2ccccc2)C(F)(F)F)cc1]

N-tosyl-1-trifluoromethyl-benzylamine

Substrate: N-tosylbenzaldimine. Conditions: LA: K(BOCH$_2$CH$_2$N)$_3$CF$_3$. 1.0 equivalents K(LA-CF$_3$) used. 0.40 mmol substrate. Reaction time: 1 hours. Quench: saturated NH$_4$Cl. Chromatography conditions: 0-100% hexane/DCM, then 0-100% DCM/ethyl acetate, 16 column volumes, 25 g SiO$_2$, flow rate 1 column volume per minute. 86 mg white solid, 65%. $^1$H-NMR (CDCl$_3$): 7.60 (ß, 2H, (d, J$_{1H-1H}$=8.2)), 7.18 (ß, α, 7H, m), 6.16 (ε, 1H, (d, J$_{1H-1H}$=9.1)), 4.91 (γ, 1H, (p, J$_{1H-19F}$=7.7)), 2.34 (η, 3H, s). $^{13}$C-NMR: 143.74, 136.89, 131.79, 129.46, 129.19, 128.74, 127.76, 126.92, 123.89 (q, J$_{13C-19F}$=282), 59.18 (q, J$_{13C-19F}$=32), 21.43. $^{19}$F-NMR: −74.02 (d, J$_{19F-1H}$=7.4). HRMS (ESI-): 328.0624 (M−H: 328.0625).

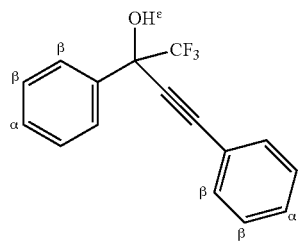 [SMILES: OC(C#Cc1ccccc1)(c1ccccc1)C(F)(F)F]

1-(Trans)-phenylethenyl-1-phenyl-trifluoromethyl-carbinol

Substrate: Trans-chalcone. Conditions: LA: K(18-crown-6)(B$_3$N$_3$Me$_6$CF$_3$)(THF). 1.0 equivalents K(LA-CF$_3$) used. 0.80 mmol substrate. Reaction time: 10 minutes. Quench: 5% HCl. Chromatography conditions: 0-100% hexane ethyl acetate, 16 column volumes, 25 g SiO$_2$, flow rate 1 column volume per minute. 190 mg colorless oil, 84%. $^1$H-NMR (CDCl$_3$): 7.69 (ß, 2H, (d, J$_{1H-1H}$=7.7)), 7.45 (ß, α, 5H, m), 7.38 (ß, 2H, (t, J$_{1H-1H}$=7.4)), 7.33 (α, 1H, (t, J$_{1H-1H}$=7.3)), 6.91 (γ, 1H, (d, J$_{1H-1H}$=16.1)), 6.77 (γ, 1H, (d, J$_{1H-1H}$=16.1)), 2.79 (ε, 1H, s). $^{13}$C-NMR: 137.40, 135.51, 133.58, 128.84, 128.76, 128.67, 128.41, 126.95, 126.84, 126.46, 125.08 (q, J$_{13C-19F}$=286), 77.34 (q, J$_{13C-19F}$=29). $^{19}$F-NMR: −78.46 (s). HRMS (EI+): 278.919 (M+: 278.0918).

1-Phenylethynyl-1-phenyl-trifluoromethylcarbinol

Substrate: Diphenylpropynone. Conditions: LA: K(18-crown-6)(B$_3$N$_3$Me$_6$CF$_3$)(THF): 1.0 equivalents K(LA-CF$_3$) used. 0.40 mmol substrate. Reaction time: 16 hours. Quench: saturated NH$_4$Cl. Chromatography conditions: 0-30% hexane ethyl acetate, 16 column volumes, 50 g SiO$_2$, flow rate 1 column volume per minute. 45 mg orange oil, 42%. $^1$H-NMR (CDCl$_3$): 7.83 (ß, 2H, (d, J$_{1H-1H}$=4.8)), 7.56 (ß, 2H, (d, J$_{1H-1H}$=4.8)), 7.46 (α, ß, 3H, m), 7.42 (α, 1H, (p, J$_{1H-1H}$=7.4)), 7.37 (ß, 2H, (t, J$_{1H-1H}$=7.4)), 3.15 (ε, 1H, s).

$^{13}$C-NMR: 135.26, 132.06, 129.55, 129.53, 128.47, 128.25, 127.19, 123.39 (q, $J_{13C-19F}$=286), 120.93, 88.09, 84.40, 73.36 (q, $J_{13C-19F}$=33). $^{19}$F-NMR: −80.29 (s). HRMS (ESI−): 275.0683 (M−H: 275.0684).

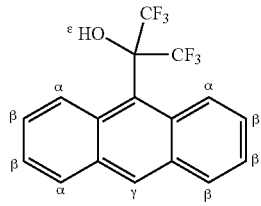 [SMILES: OC(c1c2ccccc2cc2ccccc12)(C(F)(F)F)C(F)(F)F]

1-(Anthracen-9-yl)-1,1-bistrifluoromethylcarbinol

Substrate: Anthracen-9-yl trifluoromethyl ketone. Conditions: LA: K(18-crown-6)(B$_3$N$_3$Me$_6$CF$_3$)(THF). 2.0 equivalents K(LA-CF$_3$) used. 0.40 mmol substrate. Reaction time: 1 hour. Quench: 5% HCl. Chromatography conditions: 0-100% hexane ethyl acetate, 16 column volumes, 25 g SiO$_2$, flow rate 1 column volume per minute. 120 mg yellow crystals, 87%. $^1$H-NMR (CDCl$_3$): 9.02 (α, 1H, (d, $J_{1H-1H}$=9.3)), 8.55 (α, 1H, (d, $J_{1H-1H}$=9.3)), 8.51 (γ, 1H, s), 7.99 (ß, 2H, (t, $J_{1H-1H}$=9.5)), 7.59 (ß, 1H, (t, $J_{1H-1H}$=8.3)), 7.49 (α, ß, 3H, m), 3.98 (ε, 1H, s). $^{13}$C-NMR: 134.06, 133.11, 132.46, 132.41, 131.38, 131.15, 129.39, 129.11, 127.34, 126.71, 125.98, 124.78, 124.61, 123.94 (q, $J_{13C-19F}$=290), 121.94, 83.46 (p, $J_{13C-19F}$=31). $^{19}$F-NMR: −69.31 (s). HRMS (ES+): 344.0630 (M+: 344.0636).

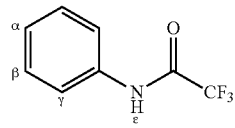 [SMILES: O=C(Nc1ccccc1)C(F)(F)F]

Phenyl trifluoroacetamide

Substrate: Phenyl isocyanate. Conditions: LA: K(18-crown-6)(B$_3$N$_3$Me$_6$CF$_3$)(THF). 1.0 equivalents K(LA-CF$_3$) used. 0.80 mmol substrate. Reaction time: 1 hour. Quench: 5% HCl. Chromatography conditions: 10-50% hexane/DCM, 8 column volumes, 25 g SiO$_2$, flow rate 1 column volume per minute. 91 mg white solid, 61%. $^1$H-NMR (CDCl$_3$): 8.03 (ε, 1H, s), 7.54 (γ, 2H, (d, $J_{1H-1H}$=7.7)), 7.46 (ß, 2H, (t, $J_{1H-1H}$=8.0), 7.23 (α, 1H, (t, $J_{1H-1H}$=7.4)). $^{13}$C-NMR: 154.87 (q, $J_{13C-19F}$=37), 135.04, 129.33, 126.39, 120.56, 115.72 (q, $J_{13C-19F}$=288). $^{19}$F-NMR: −75.80 (s). HRMS (ES+): 189.0401 (M+: 189.0401).

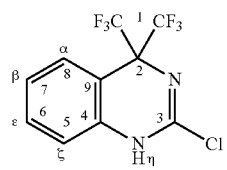

4,4-Bistrifluoromethyl-2-chloro-3-hydroquinazoline

Substrate: Dichloroquinazoline. Conditions: LA: K(18-crown-6)(B$_3$N$_3$Me$_6$CF$_3$)(THF). 1.5 equivalents K(LA-CF$_3$) used. 0.80 mmol substrate. Reaction time: 30 minutes. Quench: 10 mL 5% NaOH, then brought to pH 7 with glacial acetic acid. Chromatography conditions: 0-100% hexane/ethyl acetate, 16 column volumes, 25 g SiO$_2$, flow rate 1 column volume per minute. 146 mg light yellow solid, 60%. $^1$H-NMR (CDCl$_3$): 8.22 (η, 1H, s), 7.58 (α, 1H, (d, $J_{1H-1H}$=8.0)), 7.41 (ß, 1H, (t, $J_{1H-1H}$=7.7), 7.22 (ß, 1H, (t, $J_{1H-1H}$=7.7)), 6.88 (ζ, 1H, (d, $J_{1H-1H}$=8.0)). $^{13}$C-NMR: 145.84 (3), 135.58 (4), 131.34 (6), 128.19 (8), 125.66 (7), 122.42 (1, q, $J_{13C-19F}$=288), 115.09 (5), 108.67 (9), 73.36 (2, p, $J_{13C-19F}$=29). $^{19}$F-NMR: −73.73 (s). HRMS (ESI+): 303.0114 (M+H: 303.0124).

Assignment of the trifluoromethyl group was made based on crosspeaks in 2D NMR experiments and a septet in the 1D carbon NMR spectrum. HSQC was used to identify the carbon atoms associated with hydrogen atoms α, ß, ε, and ζ. $^{19}$F-$^{13}$C HMBC was then used to identify one bond coupling with carbon 1, two bond coupling with carbon 2, four bond coupling with carbon 3, and four bond coupling with carbon 8. Carbon 3 was assigned based on its lack of long-range coupling with any protons and high shift. The positions of carbons 9 and 4 were assigned based on their long-range coupling with hydrogen atoms α, ß, ε, and ζ. The position of carbon 8 was based on its proximity to the $^{19}$F group. Finally, the position of acidic hydrogen η and confirmation of the above assignment was obtained through single-crystal X-Ray diffraction.

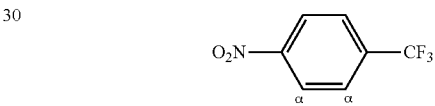

1-Trifluoromethyl-4-nitrobenzene

Substrate: 1,4-Dinitrobenzene. Conditions: LA: K(18-crown-6)(B$_3$N$_3$Me$_6$CF$_3$)(THF). 1.0 equivalents K(LA-CF$_3$) used. 0.40 mmol substrate. Reaction time: 2 hour. Quench: pure water. Chromatography conditions: 0-100% Hexane/DCM, 8 column volumes, 25 g SiO$_2$, flow rate 1 column volume per minute. 64 mg white solid, 42%. $^1$H-NMR (CDCl$_3$): 8.34 (α, 2H, (d, $J_{1H-1H}$=8.4)), 7.84 (α, 2H, (d, $J_{1H-1H}$=8.5)). $^{13}$C-NMR: 150.00, 136.06 (q, $J_{13C-19F}$=33), 126.77 (q, $J_{13C-19F}$=3), 124.07, 122.94 (q, $J_{13C-19F}$=273), 73.36 (q, $J_{13C-19F}$=33). $^{19}$F-NMR: −63.19 (s). HRMS (ES+): 191.0195 (M+: 191.0194).

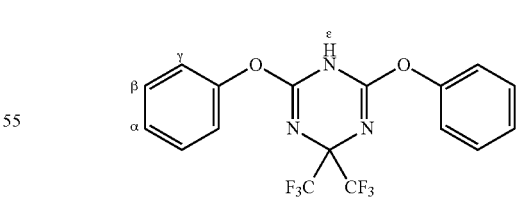

2,4-Phenoxy-6,6-bistrifluoromethyl-3-hydro-triazine

Substrate: 2,4-diphenoxy-6-chlorotriazine. Conditions: LA: K(18-crown-6)(B$_3$N$_3$Me$_6$CF$_3$)(THF). 2.0 equivalents K(LA-CF$_3$) used. 0.40 mmol substrate. Reaction time: 2 hour. Quench: pure water. Chromatography conditions: 0-50% Hexane/Ethyl acetate, 8 column volumes, 25 g SiO$_2$, flow rate 1 column volume per minute. 123 mg white solid, 76%. $^1$H-NMR (DMSO-$d_6$): 12.36 (ε, 1H, s), 7.84 (β, 2H, (t, 4H, (t, $J_{1H-1H}$=7.8)), 7.27 (α, 2H, (t, $J_{1H-1H}$=7.3)), 7.21 (γ, 4H, (d, $J_{1H-1H}$=8.0)). $^{13}$C-NMR (DMSO-$d_6$): 155.74, 151.04, 130.12, 126.60, 122.09 (q, $J_{13C-19F}$=288), 121.63, 81.02 (p, $J_{13C-19F}$=29.5). $^{19}$F-NMR: −79.44 (s). HRMS (ES+): 403.0759 (M+: 403.0755).

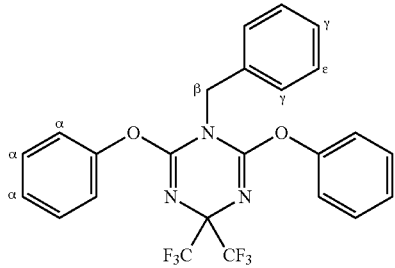 [SMILES: FC(F)(F)C1(C(F)(F)F)N=C(Oc2ccccc2)N(Cc2ccccc2)C(Oc2ccccc2)=N1]

2,4-Phenoxy-6,6-bistrifluoromethyl-3-benzyl-triazine

Substrate: 2,4-diphenoxy-6-chlorotriazine. Conditions: LA: K(18-crown-6)($B_3N_3Me_6CF_3$)(THF). 2.0 equivalents K(LA-$CF_3$) used. 0.40 mmol substrate. Reaction time: 30 minutes. Quench: 1 equiv. benzyl bromide was added under nitrogen, then the reaction stirred for 16 hours at 25° C. The reaction mixture was then quenched with 10 mL pure water. Chromatography conditions: 0-100% Hexane/Ethyl acetate, 16 column volumes, 25 g $SiO_2$, flow rate 1 column volume per minute. 108 mg white solid, 55%. $^1$H-NMR (CDCl$_3$): 7.37 (α, 10H, m), 7.24 (ε, 2H, (t, $J_{1H-1H}$=7.4)), 7.11 (γ, 3H, m), 5.21 (β, 2H, s). $^{13}$C-NMR: 153.07, 151.25, 136.53, 129.33, 128.92, 127.95, 126.86, 126.02, 121.59 (q, $J_{13C-19F}$=288), 121.11, 78.83 (p, $J_{13C-19F}$=30.3), 46.00. $^{19}$F-NMR: −80.41 (s). HRMS (ES+): 493.1229 (M+: 493.1225).

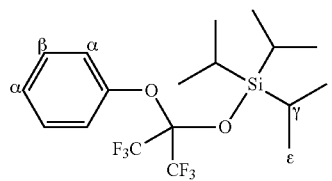 [SMILES: CC(C)[Si](OC(Oc1ccccc1)(C(F)(F)F)C(F)(F)F)(C(C)C)C(C)C]

Triisopropylsilyl Hexafluoro-2-phenoxypropan-2-ol

Substrate: Diphenylcarbonate. Conditions: LA: K(18-crown-6)($B_3N_3Me_6CF_3$)(THF). 2.0 equivalents K(LA-$CF_3$) used. 0.40 mmol substrate. Reaction time: 30 minutes. Quench: 2.0 equivalents triisopropylsilyl chloride were added, then the reaction stirred for 16 hours at 25° C. The reaction mixture was then quenched with 10 mL pure water. Chromatography conditions: 100% Hexane, 4 column volumes, 100 g $SiO_2$, flow rate 0.5 column volume per minute; chromatography repeated six times to remove triisopropylsilyl phenol, keeping pure fractions. 102 mg colorless oil, 61%. Boiling point: 65° C. at 0.080 Torr. $^1$H-NMR (CDCl$_3$): 7.32 (β, 2H, (t, $J_{1H-1H}$=8.4)), 7.19 (α, 3H, m), 1.14 (γ, 3H, m), 1.05 (ε, 18H, (d, $J_{1H-1H}$=7.2)). $^{13}$C-NMR: 151.46, 129.07, 125.80, 123.58, 120.73 (q, $J_{13C-19F}$=293), 95.20 (p, $J_{13C-19F}$=32.8), 17.43, 13.07. $^{19}$F-NMR: −76.97 (s). HRMS (ES+): 373.1061 (M-$C_3H_7^+$: 373.1059).

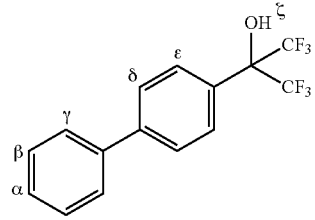 [SMILES: OC(c1ccc(-c2ccccc2)cc1)(C(F)(F)F)C(F)(F)F]

1,1-bistrifluoromethyl-1-(4-phenyl)phenyl-methanol

Substrate: Biphenyl-4-carbonyl chloride. Conditions: LA: K(18-crown-6)($B_3N_3Me_6CF_3$)(THF). 2.2 equivalents K(LA-$CF_3$) used. 0.40 mmol substrate. Reaction time: 16 hours. Quench: 5% HCl. Chromatography conditions: 0-20% Hexane/Ethyl acetate, 8 column volumes, 25 g $SiO_2$, flow rate 1 column volume per minute. 107 mg white solid, 84%. $^1$H-NMR (CDCl$_3$): 7.82 (ε, 2H, (d, $J_{1H-1H}$=8.1)), 7.71 (δ, 2H, (d, $J_{1H-1H}$=8.2)), 7.64 (γ, 2H, (d, $J_{1H-1H}$=7.8)), 7.49 (β, 2H, (t, $J_{1H-1H}$=7.5)), 7.41 (α, 1H, (t, $J_{1H-1H}$=7.3)), 3.38 (ζ, 1H, s). $^{13}$C-NMR: 143.16, 139.88, 128.90, 128.06, 127.94, 127.30, 127.20, 126.94, 122.65 (q, $J_{13C-19F}$=288), 77.18 (p, $J_{13C-19F}$=30.3) (overlap with CDCl$_3$). $^{19}$F-NMR: −75.58 (s). HRMS (ES+): 320.0636 (M-$C_3H_7^+$: 320.0636).

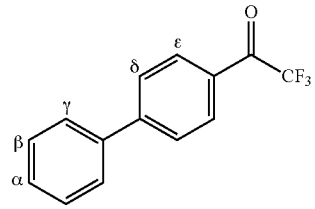 [SMILES: O=C(c1ccc(-c2ccccc2)cc1)C(F)(F)F]

1,1-Bistrifluoromethyl-1-(4-phenyl)phenyl-methanol

Substrate: Methyl biphenyl-4-carboxylate. Conditions: LA: K(18-crown-6)($B_3N_3Me_6CF_3$)(THF). 1.0 equivalents K(LA-$CF_3$) used. 0.40 mmol substrate. Reaction time: 30 minutes. Quench: 5% HCl. Chromatography conditions: 0-100% Hexane/Ethyl acetate, 8 column volumes, 25 g $SiO_2$, flow rate 1 column volume per minute. 29 mg white solid, 29%. $^1$H-NMR (CDCl$_3$): 8.17 (ε, 2H, (d, $J_{1H-1H}$=8.0)), 7.78 (δ, 2H, (d, $J_{1H-1H}$=8.4)), 7.66 (γ, 2H, (d, $J_{1H-1H}$=7.1)), 7.51 (β, 2H, (t, $J_{1H-1H}$=7.6)), 7.45 (α, 1H, (t, $J_{1H-1H}$=7.4)). $^{13}$C-NMR: 180.07 (q, $J_{13C-19F}$=35.0), 148.21, 139.11, 130.72, 129.11, 128.89, 128.56, 127.63, 127.34, 116.76 (q, $J_{13C-19F}$=291). $^{19}$F-NMR: −71.35 (s). HRMS (ES+): 250.0611 (M+: 250.0605).

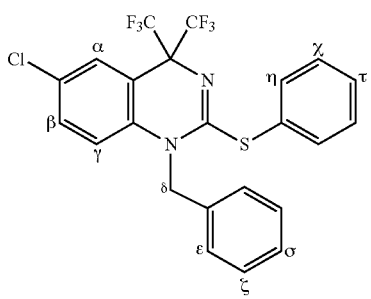 [SMILES: FC(F)(F)C1(C(F)(F)F)N=C(Sc2ccccc2)N(Cc2ccccc2)c2ccc(Cl)cc21]

1-benzyl-6-chloro-2-(phenylthio)-4,4-bis(trifluoromethyl)-14-dihydroquinazoline

Substrate: Trichloroquinazoline. Experimental: Trichloroquinazoline (0.4 mmol, 93.4 mg) was combined with 2 equivalents K(18-crown-6)(B$_3$N$_3$Me$_6$CF$_3$)(THF) (0.8 mmol, 4 mL, 0.2M solution in THF) and stirred for 30 minutes at 25° C. One equivalent benzyl bromide (0.4 mmol, 68.4 mg) was then added, and the mixture stirred at 70° C. for 24 hours. The reaction was then cooled to 25° C., and 1 equivalent sodium thiophenolate (0.4 mmol, 52.8 mg) was added. The reaction was then heated to 70° C. and stirred for 24 hours. The THF solvent was then removed by rotary evaporation, and the crude solid purified by flash chromatography (conditions: 25 g SiO$_2$ column, 0-50% DCM/Hexane over 16 column volumes at a flow rate of 1 column volume per minute) to afford 120 mg of white solid (60%). $^1$H-NMR (CDCl$_3$): 7.55 (η, 2H, overlap), 7.54 (1H, α, overlap), 7.41 (5H, χ, τ, ζ, overlap), 7.34 (1H, σ, (t, $J_{1H-1H}$=7.4)), 7.28 (2H, ε, (d, $J_{1H-1H}$=7.7)), 7.24 (1H, (d(d), ($J_{1H-1H}$=8.8, 2.1)), 6.75 (1H, γ, (d, $J_{1H-1H}$=9.0)), 5.27 (2H, δ, s). $^{13}$C-NMR: 158.99, 136.80, 135.69, 134.95, 130.81, 129.48, 129.37, 129.21, 128.73, 128.08, 127.93, 125.76, 122.46 (q, $J_{13C-19F}$=288), 115.67, 113.23, 66.80 (p, $J_{13C-19F}$=28.7), 50.36. $^{19}$F-NMR: −73.92 (s). HRMS (ESI+): 501.0619 (M+H: 501.0621).

Small Molecules

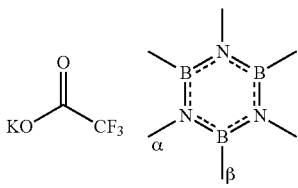

Potassium Trifluoroacetate

K(B$_3$N$_3$Me$_6$)CF$_3$ (2 mmol, 0.2 M stock in DMSO) was placed in a Fisher-Porter tube with a small stirbar. The vessel was charged with 60 psi carbon dioxide, and stirred. A pressure drop to 56 psi was observed along with the precipitation of copious white solid. The reaction was stirred at room temperature for 12 hours. After this time, the reaction mixture was extracted with pentane (3×10 mL). The combined pentane extracts were dried over anhydrous calcium chloride to remove trace DMSO, then filtered and evaporated under high vacuum to afford hexamethylborazine in 95% yield (314 mg, 1.91 mmol). $^1$H-NMR (CDCl$_3$): 2.86 (α, 9H, s), 0.47 (β, 9H, s). $^{13}$C-NMR: 34.52, 0.03 (broad). $^{11}$B-NMR: 36.52 (s). HRMS (ES+): 165.1781 (M+: 165.1780).

Recovered Hexamethylborazine:

The DMSO phase was evaporated overnight at 25° C. in a sublimation apparatus with a coldfinger cooled to 2° C. under dynamic vacuum (0.1 mTorr). The residual solid was then extracted into water, and this was then carefully dried in a scintillation vial to give potassium trifluoroacetate as an off-white solid in 93% yield (285 mg, 1.86 mmol). $^{13}$C{$^{19}$F}-NMR (D$_2$O): 162.90, 116.32. $^{19}$F-NMR (D$_2$O): −75.40 (s).

Potassium Trifluoroacetate:

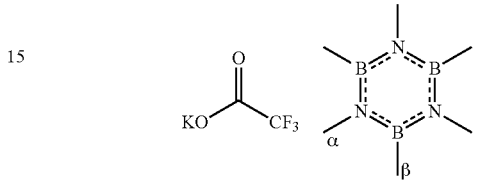

Trimethylsilyl CF$_3$:

Hexamethylborazine (7.7 mmol, 1.262 g) and 15-crown-5 (7.7 mmol, 1.696 g) were suspended in 37 mL DMSO in a 500 mL schlenk flask equipped with a large teflon-coated magnetic stirbar, valved stopcock topped with a septum, and a valved sidearm connected to a series of traps held at 0° C., −80° C., −120° C., and −200° C. which were connected to a vacuum line. The following operations were then carried out:

Step 1: NaDMSO (7.0 mmol, 1.7M, 4.2 mL) was then added, and the reaction was stirred for 30 minutes to generate Na(15-crown-5)(B$_3$N$_3$Me$_6$) DMSO. Step 2: HCF$_3$ (220 mL, 1.2 equiv., 8.4 mmol) was then added to the reaction at 15° C. over the course of 5 minutes. The reaction was then stirred for 5 minutes. Step 3: TMSCl (7.6 mmol, 0.964 mL) was then added to the reaction over the course of 1 minute, then stirred for four minutes. Step 4: The inert gases in the apparatus were withdrawn through the series of low temperature traps until a static vacuum of 0.070 mTorr or better was obtained. The volatiles were distilled under vacuum with the reaction flask held at 15° C. for 30 minutes, then for a further hour with the reaction flask held at 25° C.

Steps 1 through 4 were then repeated ten times. The contents of the −80° C. and −120° C. traps were then combined and analyzed by $^1$H NMR, which showed 49% conversion of all TMSCl used to TMSCF$_3$ and 51% conversion of TMSCl to TMS$_2$O. These were then separated to provide 2.82 g of pure TMSCF$_3$ (27% isolated yield) as a colorless oil via fractional distillation (b.p.: 54° C.).

KSO$_2$CF$_3$:

Hexamethylborazine (7.7 mmol, 1.262 g) was suspended in 37 mL DMSO in a 500 mL schlenk flask. KDMSO (7.0 mmol, 2.0 M) was then added, and the reaction was stirred for 30 minutes to generate K(B$_3$N$_3$Me$_6$) DMSO. Step 2: HCF$_3$ (220 mL, 1.2 equiv., 8.4 mmol) was then added to the reaction at 25° C. over the course of 5 minutes. The reaction was then stirred for 5 minutes. SO$_2$ (220 mL, 1.2 equiv., 8.4 mmol) was then added to the reaction over the course of 1 minute, then stirred for four minutes. Hexamethylborazine was recovered from the reaction mixture by extraction with pentane in 98% yield. The DMSO was then removed by vacuum distillation to provide KSO$_2$CF$_3$ in >95% yield with 20% contamination with DMSO. This solid was then washed with DCM to provide 966 mg of KSO$_2$CF$_3$ in 80% yield.

Togni Reagent 1:

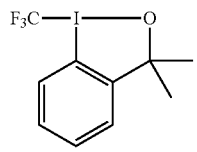

Hexamethylborazine (2.7 mmol, 0.443 g) and 18-crown-6 (2.7 mmol, 0.712 g) were dissolved in 11 mL THF in a 20 mL single-neck conical flask equipped with a large teflon-coated magnetic stirbar. The vessel was then allowed to cool to 0° C. in a glovebox cold-well for one hour with gentle stirring. Benzylpotassium (2.7 mmol, 0.350 g) was then quickly added to this cold solution, and the initial deep red color of dissolved benzylpotassium quickly changed to a faint purple color. The homogeneous solution was stirred for 10 minutes, giving a homogeneous purple solution. The flask was then sealed with a tightly belt-clamped septum. Gaseous $HCF_3$ was added to the sealed vessel with a 60 mL syringe (3.3 mmol, 75 mL) and continuous efficient stirring. The faint pink homogeneous solution was stirred for 10 minutes. 1 equivalent 1-chloro-3,3-dimethyl-1,3-dihydro-1λ-benzo[d][1,2]iodaoxole was then added to the reaction mixture dissolved in THF at 0° C. The reaction mixture was then evaporated, reconstituted in 10 mL acetonitrile, and the hexamethylborazine recovered via extraction with pentane. The residue was then evaporated and subjected to sublimation, with the product iodonium $CF_3$ salt subliming at 40° C. to provide the product.

What is claimed:

1. A complex having a structure of formula (I):

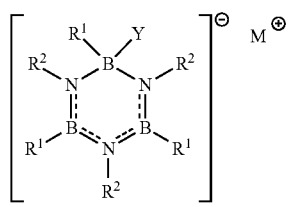

(I)

wherein $R^1$ is $C_{1-8}$alkyl, $C_{1-8}$alkoxy, aryl, $C_{3-8}$cycloalkyl, or $NR^3R^4$;

$R^2$ is $C_{1-8}$alkyl, aryl, or $C_{3-8}$cycloalkyl;

or $R^1$ and $R^2$ taken together with the atoms to which they are attached form an optionally substituted 5-7-membered ring;

$R^3$ and $R^4$ are each independently H or $C_{1-8}$alkyl, or $R^3$ and $R^4$ taken together with the N atom form a 3-5-membered ring;

Y is a $C_{1-8}$perfluoroalkyl; and

M is a counterion.

2. The complex of claim 1, wherein $R^1$ and $R^2$ taken together with the atoms to which they are attached form a 5-6-membered ring.

3. The complex of claim 1, wherein the complex is chiral.

4. The complex of claim 1, wherein Y comprises one or more $^{18}F$ atoms.

5. The complex of claim 1, wherein Y is a $C_{1-3}$perfluoroalkyl.

6. The complex of claim 5, wherein Y is $CF_3$, $CHF_2$, or $C_2F_5$.

7. A composition comprising the complex of claim 1 and a crown ether.

8. The composition of claim 7, wherein the crown ether is 18-crown-6 or 15-crown-5.

9. The complex of claim 1 having a structure selected from the group consisting of:

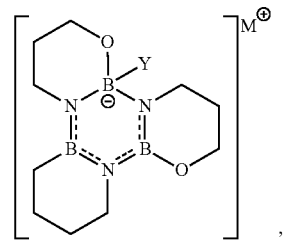

,

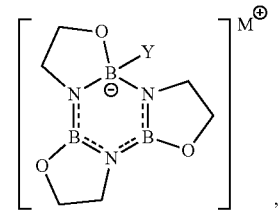

,

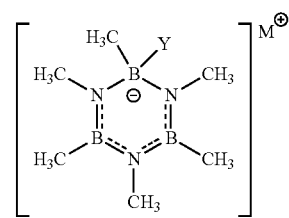

,

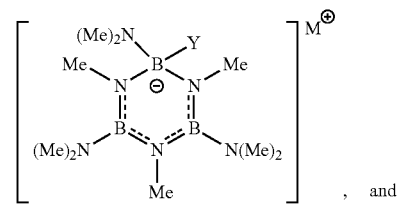

, and

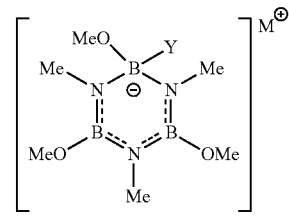

.

10. A method comprising:

contacting a base, a Lewis acid, and a H—$C_{1-8}$perfluoroalkane to form a complex of the Lewis acid and $C_{1-8}$perfluoroalkane;

wherein the Lewis acid has a structure of formula (II):

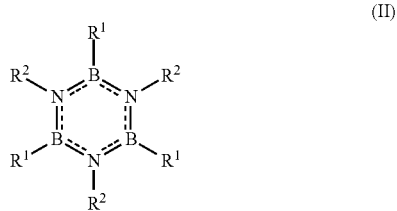

R$^1$ is C$_{1-8}$alkyl, C$_{1-8}$alkoxy, aryl, C$_{3-8}$cycloalkyl, or NR$^3$R$^4$;

R$^2$ is C$_{1-8}$alkyl, aryl, or C$_{3-8}$cycloalkyl; or

R$^1$ and R$^2$ taken together with the atoms to which they are attached form an optionally substituted 5-7-membered ring; and R$^3$ and R$^4$ are each independently H or C$_{1-8}$alkyl, or R$^3$ and R$^4$ taken together with the N atom form a 3-5 membered ring.

11. The method of claim 10, wherein the base is KDMSO, NaDMSO, KOC(CH$_3$)$_3$, KCH$_2$Ph, KH, NaH, or a mixture thereof.

12. The method of claim 10, wherein the Lewis acid is

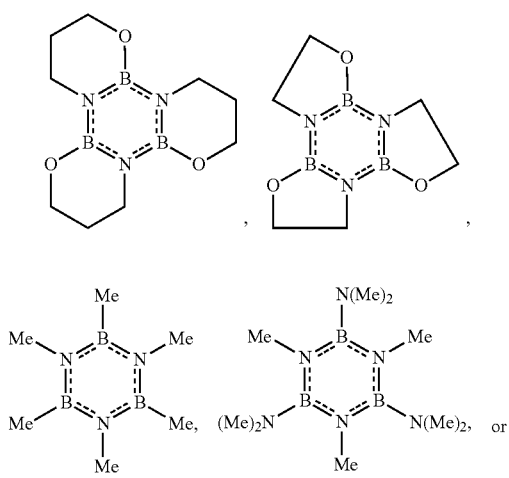

13. The method of claim 10, further comprising perfluoroalkylating an aromatic or heteroaromatic compound by admixing a complex of Formula (I) with the aromatic or heteroaromatic compound to form a perfluoroalkylaromatic or perfluoroalkylheteroaromatic compound, wherein the aromatic or heteroaromatic compound comprises a keto, formyl, ester, anhydride, carbonate, isocyanate, thioisocyanate, acyl chloride, or imino substituent or a halo or nitro substituent, and the complex of Formula (I) has the following structure:

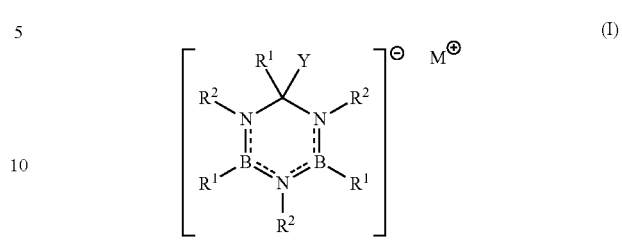

wherein

R$^1$ is C$_{1-8}$alkyl, C$_{1-8}$alkoxy, aryl, C$_{3-8}$cycloalkyl, or NR$^3$R$^4$;

R$^2$ is C$_{1-8}$alkyl, aryl, or C$_{3-8}$cycloalkyl;

or R$^1$ and R$^2$ taken together with the atoms to which they are attached form an optionally substituted 5-7-membered ring;

R$^3$ and R$^4$ are each independently H or C$_{1-8}$alkyl, or R$^3$ and R$^4$ taken together with the N atom form a 3-5-membered ring;

Y is a C$_{1-8}$perfluoroalkyl; and

M is a counterion.

14. The method of claim 13, wherein the heteroaromatic compound comprises a pyridine, quinoline, pyrimidine, or triazine ring and comprises a keto, formyl, ester, anhydride, carbonate, isocyanate, thioisocyanate, acyl chloride, or imino substituent or a halo or nitro substituent.

15. The method of claim 10, further comprising reacting the complex with a reagent to form a perfluoroalkylating reagent and to regenerate the Lewis acid, wherein the reagent is selected from the group consisting of P(Ar)$_2$L, Pd(TMEDA)(Ar)L, ZnL$_2$, Zn(TMEDA)L$_2$, Bi(L)$_3$, Ph$_2$S$_2$, Ph$_2$Se$_2$, LCN, CO$_2$, CuL, AgL, SnMe$_3$L, PbMe$_3$L, Au(iPr)L, S$_8$, trialkylsilyl-L, SO$_2$, an iodonium(III) reagent, Te, and Se; each L independently is Cl, Br, I, NO$_3$, OSO$_2$Ar, or OSO$_2$CF$_3$; and Ar is aryl.

16. The method of claim 15, wherein the iodonium reagent is

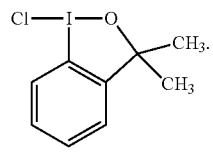

and the perfluoroalkylating reagent is

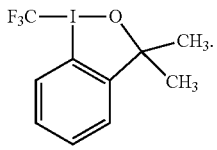

17. The method of claim 15, wherein the perfluoroalkylating reagent is P(Ar)$_2$CF$_3$, Zn(CF$_3$)$_2$, Pd(TMEDA)(Tol)CF$_3$, CuCF$_3$, AgCF$_3$, SnMe$_3$CF$_3$, SiMe$_3$CF$_3$, PbMe$_3$CF$_3$, Au(iPr)CF$_3$, Zn(TMEDA)(CF$_3$)$_2$, Bi(CF$_3$)$_2$ Cl, PhSCF$_3$, PhSeCF$_3$, BrCF$_3$, CO$_2$CF$_3$, SO$_2$CF$_3$, SCF$_3$, TeCF$_3$, or SeCF$_3$.

18. The method of claim 10, wherein the contacting occurs in a polar, aprotic solvent.

19. The method of claim 13, wherein the aromatic or heteroaromatic compound is an $NO_2$- or Cl-substituted aromatic compound (Ar—$NO_2$ or Ar—Cl) or $NO_2$- or Cl-substituted heteroaromatic compound (Het-$NO_2$ or Het-Cl) and the $NO_2$- or Cl-substituent is substituted for the perfluoroalkyl group to form Ar-perfluoroalkyl or Het-perfluoroalkyl.

* * * * *

UNITED STATES PATENT AND TRADEMARK OFFICE
CERTIFICATE OF CORRECTION

PATENT NO. : 10,519,172 B2
APPLICATION NO. : 16/308304
DATED : December 31, 2019
INVENTOR(S) : Szymczak et al.

It is certified that error appears in the above-identified patent and that said Letters Patent is hereby corrected as shown below:

In the Claims

At Column 42, Lines 13-24, " 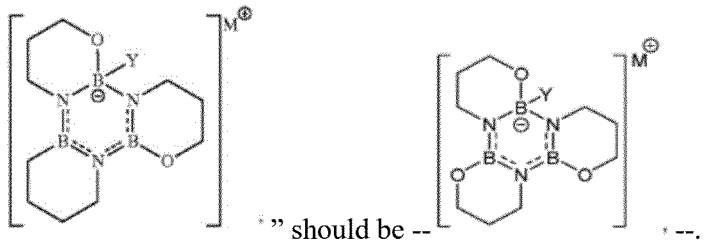 " should be -- 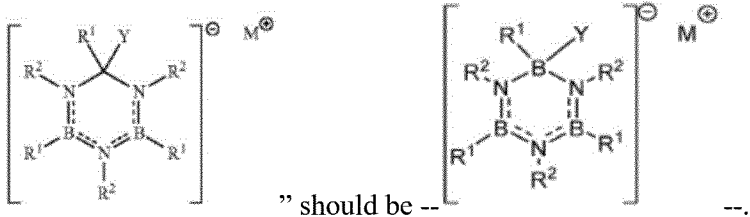 --.

At Column 44, Lines 5-14, " 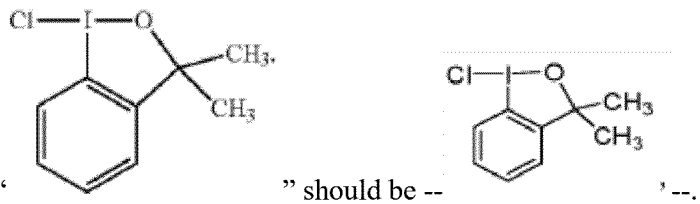 " should be --  --.

At Column 44, Lines 42-48, "  " should be --  --.

Signed and Sealed this
Eighth Day of February, 2022

Drew Hirshfeld
*Performing the Functions and Duties of the
Under Secretary of Commerce for Intellectual Property and
Director of the United States Patent and Trademark Office*